United States Patent
Simpson, Jr.

(10) Patent No.: US 9,364,462 B2
(45) Date of Patent: Jun. 14, 2016

(54) ALPHA-1-ADRENERGIC RECEPTOR AGONIST THERAPY

(71) Applicant: The Regents of the University of California, Oakland, CA (US)

(72) Inventor: Paul C. Simpson, Jr., San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/067,774

(22) Filed: Oct. 30, 2013

(65) Prior Publication Data

US 2014/0121257 A1    May 1, 2014

Related U.S. Application Data

(60) Provisional application No. 61/720,201, filed on Oct. 30, 2012.

(51) Int. Cl.
*A61K 31/4164* (2006.01)

(52) U.S. Cl.
CPC .................. *A61K 31/4164* (2013.01)

(58) Field of Classification Search
None
See application file for complete search history.

(56) References Cited

U.S. PATENT DOCUMENTS

| | | |
|---|---|---|
| 4,634,705 A | 1/1987 | DeBernardis et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,610,174 A | 3/1997 | Craig et al. |
| 5,620,993 A | 4/1997 | Patane et al. |
| 6,323,231 B1 | 11/2001 | Brioni et al. |
| 6,726,920 B1 | 4/2004 | Theeuwes et al. |
| 2001/0039255 A1 | 11/2001 | Brioni et al. |
| 2005/0287565 A1* | 12/2005 | Merchiers et al. ............. 435/6 |
| 2010/0113377 A1* | 5/2010 | Simpson ................... 514/34 |

FOREIGN PATENT DOCUMENTS

WO    WO 96/05309 A2    2/1996

OTHER PUBLICATIONS

Goldstein, Primary Prevention of Ischemic Stroke: A Statement for Healthcare Professionals From the Stroke Council of the American Heart Association, Circulation, 2001, 103, pp. 163-182.*
Rank, Adrenergic Receptors Modulate Motoneuron Excitability, Sensory Synaptic Transmission and Muscle Spasms After Chronic Spinal Cord Injury, J. Neurophysiol., published Nov. 3, 2010, 105, pp. 410-422.*
Shelton, Effect of Lesion Location on Upper Limb Motor Recovery After Stroke, Stroke, 2001, pp. 107-112.*
Aries et al., "Essential role of GATA-4 in cell survival and drug-induced cardiotoxicity", *PNAS*, 101(18):6975-6980 (2004).

(Continued)

*Primary Examiner* — San-Ming Hui
*Assistant Examiner* — Andrew Lee
(74) *Attorney, Agent, or Firm* — Mintz Levin Cohn Ferris Glovsky and Popeo, P.C.

(57) ABSTRACT

Presented herein inter alia are novel methods of treating heart and brain diseases.

10 Claims, 20 Drawing Sheets

(56) References Cited

OTHER PUBLICATIONS

Chan, Trevor, "Alpha1A-Adrenergic Receptor Agonist Therapy Activated Survival Signaling in Cardiac Myocytes and Prevents Doxorubicin-Induced Cardiomyopathy", Poster Abstract from Sarnoff Cardiovascular Research Foundation, Proceedings of the 28th Annual Scientific Meeting, Georgetown University Conference Center, Washington, DC, May 1-4 (2008).

Dash et al., "A Molecular MRI Probe to Detect Treatment of Cardiac Apoptosis In Vivo", *Magnetic Resonance in Medicine*, 66:1152-1162 (2011).

Doze et al., "Long-Term $\alpha_1$-Adrenergic Receptor Stimulation Improves Synaptic Plasticity, Cognitive Function, Mood, and Longevity", *Molecular Pharmacology*, 80(4):747-758 (2011).

Evans et al., "Quantification of Functional Selectivity at the Human $\alpha_1$-Adrenoceptor", *Molecular Pharmacology*, 79(2):298-307 (2011).

Gan et al., "Inhibition of Phenylephrine-Induced Cardiomyocyte Hypertrophy by Activation of Multiple Adenosine Receptor Subtypes", *The Journal of Pharmacology and Experimental Therapeutics*, 312:27-34 (2005).

Graham et al., "$\alpha_1$-Adrenergic Receptor Subtypes: Molecular Structure, Function and Signaling", *Circulation Research*, 78:737-749 (1996).

Hosoda et al., "Two $\alpha_1$-Adrenergic Receptor Subtypes Regulating the Vasopressor Response have Differential Roles in Blood Pressure Regulation", *Molecular Pharmacology*,67:912-922 (2006).

Huang et al., "An $\alpha_1$A-Adrenergic-Extracellular Signal-Regulated Kinase Survival Signaling Pathway in Cardiac Myocytes", *Circulation*, 115:763-772 (2007).

Jensen et al., "Alpha-1-adrenergic receptors: Targets for agonist drugs to treat heart failure", *Journal of Molecular and Cellular Cardiology*, 51:518-528 (2011).

Knepper et al., "A-61603, a Potent $\alpha_1$-Adrenergic Receptor Agonist, Selective for the alpha 1A Receptor Subtype", *The Journal of Pharmacology and Environmental Therapeutics*, 274:97-103 (1995).

Merriam-Webster's Third New International Dictionary, Dec. 2000, 5 pages.

Myagmar et al., "Abstract 15769: Alpha1A-Adrenergic Receptors in Neuroprotection" [http://circ.ahajournals.org/cgi/content/meeting_abstract/124/21_MeetingAbstracts/A15769] *Circulation, AHA Journals* (2011) Retrieved from the Internet on Jul. 23, 2012, 1 page.

O'Connell et al., "$\alpha_1$-Adrenergic Receptors Prevent a Maladaptive Cardiac Response to Pressure Overload", *J.Clin. Invest.*, 116:1005-1015 (2006).

Rokosh et al., "$\alpha_1$-Adrenergic Receptor Subtype mRNAs are Differentually Regulated by $\alpha_1$-Adrenergic and other Hypertrophic Stimuli in Cardiac Myocytes in Culture and In Vivo", *The Journal of Biological Chemistry*, 271(10):5839-5843 (1996).

Rokosh et al., "Knockout of the $\alpha_1$A/C-Adrenergic Receptor Subtype: The $\alpha_1$A/C is Expressed in Resistance Arteries and is Required to Maintain Arterial Blood Pressure", *PNAS*, 99(14):9474-9479 (2002).

Rorabaugh et al., "$\alpha_{1A}$-but not $\alpha_{1B}$• Adrenergic Receptors Precondition the Ischemic Heart by a Staurosporine-Sensitive, Chelerythrine-Insensitive Mechanism", *Cardiovascular Research*, 65:436-445 (2005).

Shibata et al., "$\alpha_1$-Adrenergic Receptor Subtyoes Differentually Control the Cell Cycle of Transfected CHO Cells through a cAMP-Dependent Mechanism Involving p27$^{kip1}$", *The Journal of Biological Chemistry*, 278(1):672-678 (2003).

Woodcock et al., "Cardiac $\alpha_1$-Adrenergic Drive in Pathological Remodelling", *Cardiovasular Research*, 77:452-462 (2008).

* cited by examiner

| Cardiomyopathy Model | A61603 (10 ng/kg/d) Effects on the Main CM End-points | | | | | |
|---|---|---|---|---|---|---|
| | Survival | Cardiac Function | Hypertrophy | Apoptosis | Necrosis | Fibrosis |
| Toxic (doxorubicin) | increased | improved | no change | decreased | decreased | decreased |
| Ischemic, post-MI (small MI) | na | improved | increased (myocyte) | no change | no change | decreased |
| Ischemic, post-MI (large MI) | nt | improved (acute α1) | nt | nt | nt | nt |
| LV pressure overload (TAC) | na | improved | decreased (LV) | nt | nt | decreased (collagen I) |
| RV pressure overload (bleomycin inhalation) | na | improved | decreased (RV) | nt | nt | nt |

Figure 12

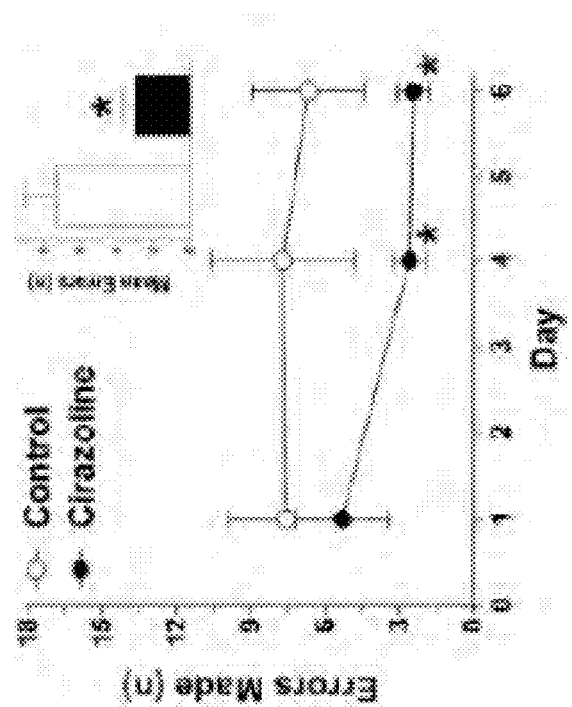
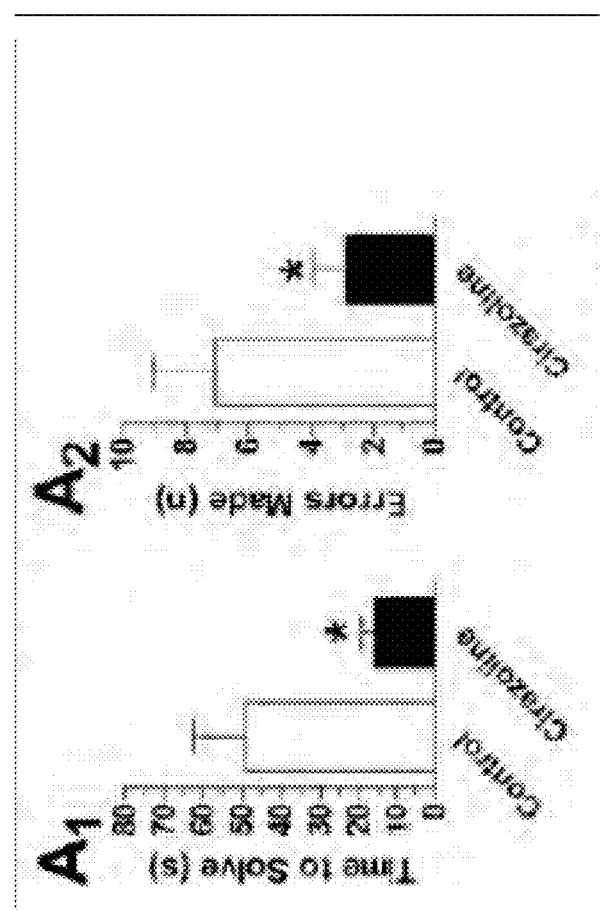
Figure 18

ALPHA-1-ADRENERGIC RECEPTOR AGONIST THERAPY

CROSS-REFERENCES TO RELATED APPLICATIONS

This application claims the benefit of U.S. Provisional Patent Application No. 61/720,201, filed Oct. 30, 2012, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant no. HL31113 awarded by the National Institutes of Health. The Government has certain rights in the invention.

BACKGROUND OF THE INVENTION

Most drugs for treating heart muscle disease are antagonists or inhibitors, such as beta-adrenergic blockers, or angiotensin converting enzyme inhibitors, or aldosterone or angiotensin receptor blockers. The basic rationale for using these antagonists is to block cellular pathways that are toxic or harmful to the cell. These drugs may be effective in conditions such as heart failure, but their efficacy is limited. At the present time, no drugs are commonly used, which take the approach of activating cellular pathways that are beneficial or helpful to the cell. Alpha-1-adrenergic receptor agonists in current clinical use are designed to stimulate smooth muscle contraction, for example to treat hypotension or urinary incontinence, and are used in amounts that result in smooth muscle contraction. Such smooth muscle contraction may not be beneficial for patients with many heart or brain related diseases. The present invention provides solutions to these and other problems in the art.

BRIEF SUMMARY OF THE INVENTION

In a first aspect is provided a method of treating or preventing cardiomyopathy in a patient in need of such treatment, the method including administering a therapeutically or prophylactically effective amount of A61603, or an analog, pharmaceutically acceptable salt, or prodrug thereof.

In a second aspect is provided a method of treating or preventing brain damage in a patient in need of such treatment, the method including administering a therapeutically or prophylactically effective amount of A61603, or an analog, pharmaceutically acceptable salt, or prodrug thereof.

In a third aspect is provided a method of improving one or more cognitive capabilities in a patient in need of such treatment, the method including administering an effective amount of A61603, or an analog, pharmaceutically acceptable salt, or prodrug thereof.

In a fourth aspect is provided a method of treating or preventing heart failure in a patient in need of such treatment, the method including administering a therapeutically or prophylactically effective amount of A61603, or an analog, pharmaceutically acceptable salt, or prodrug thereof.

In a fifth aspect is provided a method of improving (e.g. increasing) heart contraction in a patient in need of such treatment, the method including administering a therapeutically effective amount of A61603, or an analog, pharmaceutically acceptable salt, or prodrug thereof.

BRIEF DESCRIPTION OF THE DRAWINGS

FIG. 12. Summary of Cardiomyopathy Studies with A61603. The Table summarizes current data with A61603 at the low dose 10 ng/kg/d in the different cardiomyopathy models. Shown are the key outcomes (survival and cardiac function) and the main cell mechanisms (hypertrophy, apoptosis, necrosis, fibrosis). nt=not tested, na=not applicable.

FIG. 18. Long-term alpha-1A agonist therapy improves learning and memory. Normal WT mice were treated 9 months with the alpha-1A agonist cirazoline, 10 mg/L in drinking water, and learning and memory were tested versus control mice using the Barnes maze. Left. In learning trials, cirazoline-treated mice were faster to solve and made fewer errors. Right. Findings were similar in memory trials (showing Errors made).

DETAILED DESCRIPTION OF THE INVENTION

I. Definitions

Figure 1:
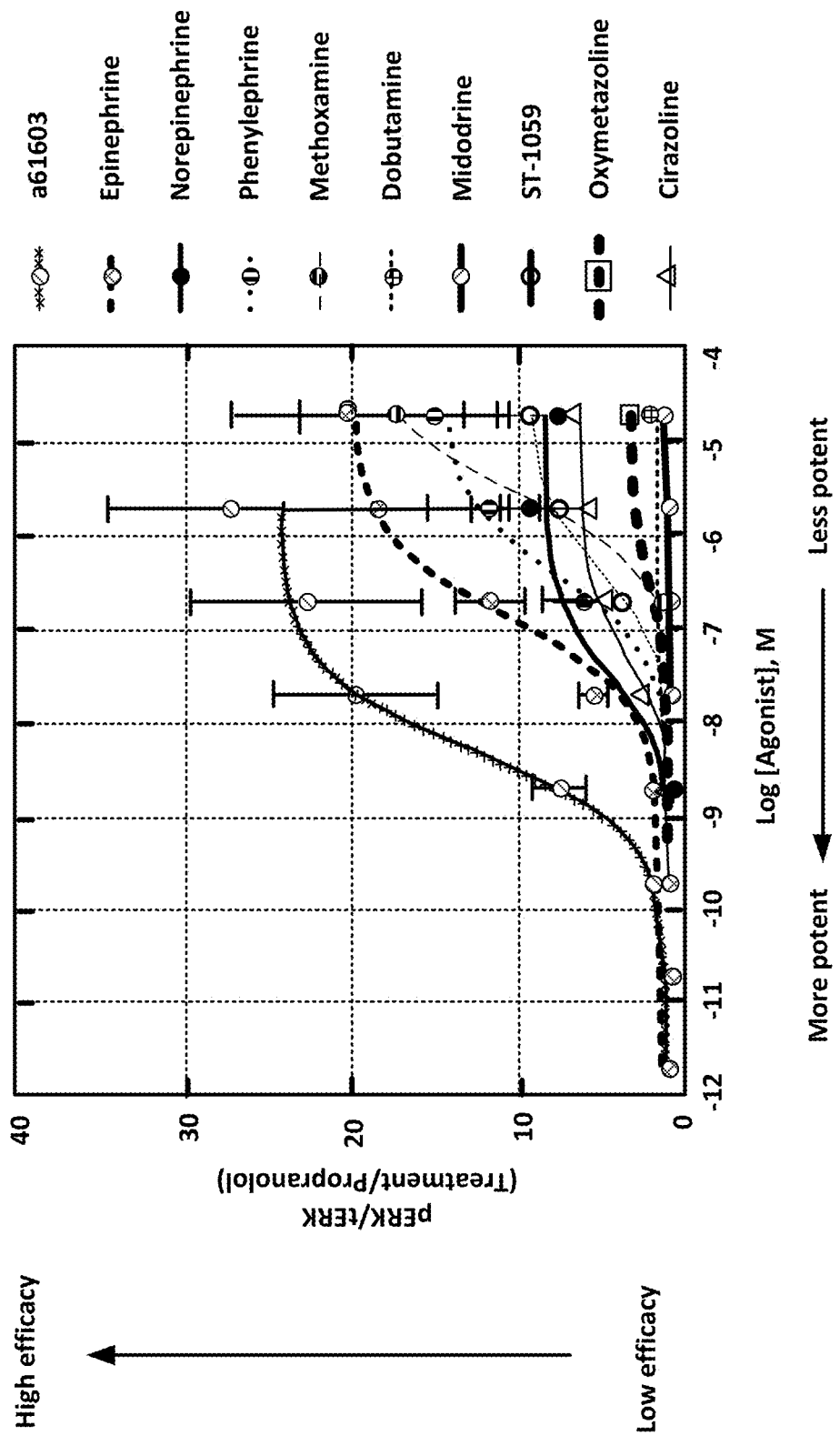
FIG. 1. A61603 protects neonatal cardiac muscle cells. A61603 activates the kinase ERK, known to be cardioprotective, with high efficacy and potency, in neonatal rat cardiac muscle cells in vitro.

The abbreviations used herein have their conventional meaning within the chemical and biological arts. The chemical structures and formulae set forth herein are constructed according to the standard rules of chemical valency known in the chemical arts.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine. and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds, agents, or drugs of the invention. One of skill in the art will recognize that other pharmaceutical excipients are useful in the present invention.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

In addition to salt forms, the present invention provides compounds, which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be converted to the compounds of the present invention when placed in a transdermal patch reservoir with a suitable enzyme or chemical reagent. In some embodiments, prodrugs of the compounds described herein (also referred to herein as "compound of the present invention") may be used in the methods described herein (including embodiments).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. Certain compounds of the present invention can exist in polymorphic forms. In general, all physical forms are equivalent for the uses contemplated by the present invention and are intended to be within the scope of the present invention.

Certain compounds of the present invention (e.g. A61603) possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds (e.g. A61603) in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, a compound described herein is also meant to include all stereochemical forms of the compound; i.e., the R and S configurations for each asymmetric center. Therefore, single stereochemical isomers as well as enantiomeric and diastereomeric mixtures of the present compounds (e.g. A61603) are within the scope of the invention.

Unless otherwise stated, compound described herein are also meant to include compounds which differ only in the presence of one or more isotopically enriched atoms. For example, compounds described herein with replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

The term "modulator" refers to a composition that increases or decreases the level of a target molecule or the function of a target molecule or the level or function of a target cell (e.g. a target may be α1 adrenergic receptor (e.g. α1A-AR) and the function to be increased or decreased may be receptor activation or downstream signaling from the receptor (e.g. Erk protein or pathway) or a target may be a cardiac cell or brain cell and the modulator may increase or decrease the level or number of cells or modulate the health or survival of the cell). In some embodiments, a modulator is a compound that reduces the severity of one or more symptoms of a disease (e.g. loss of cell function, loss of cells). In some embodiments, a modulator reduces the deterioration of heart muscle cells or heart muscle cell function. In some embodiments, a modulator reduces the deterioration of brain cells or brain cell function.

The term "preparation" is intended to include the formulation of the active agents (e.g. compound, drug) with material as a carrier providing a dosage form in which the active component with or without other carriers, is associated with a carrier. Similarly, cachets and lozenges are included. Tablets, powders, capsules, pills, cachets, and lozenges can be used as solid dosage forms suitable for oral administration.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cardiomyopathy by decreasing the incidence of cardiomyopathy and/or preventing, stopping, reversing, or slowing the development of cardiomyopathy. For example, the certain methods presented herein successfully treat brain damage by decreasing the incidence of brain cell death or brain cell loss and/or slowing the loss of brain cells or cognitive function or brain function. For example, the certain methods presented herein successfully improve cognitive capability by improving the rate of learning or improving memory or improving performance on a test of mental capability, memory, or learning. The term "treating," and conjugations thereof, include prevention of an injury, pathology, condition, or disease (e.g. cardiomyopathy, brain damage, loss of cognitive function). In embodiments treating is preventing. In embodiments, treating does not include preventing.

An "effective amount" is an amount sufficient to accomplish a stated purpose (e.g. achieve the effect for which it is administered, treat a disease, increase enzyme activity, reduce one or more symptoms of a disease or condition, improve cognitive function or capabilities). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom (s), or elimination of the symptom(s). A "prophylactically effective amount" of an agent (e.g. compound, drug, or A61603) is an amount of an agent (e.g. compound, drug, or A61603) that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of an agent (e.g. compound, drug, antagonist, or A61603) required to decrease the activity of an enzyme relative to the absence of the agent (e.g. compound, drug, antagonist, or A61603). A "function disrupting amount," as used herein, refers to the amount of an agent (e.g. compound, drug, antagonist, or A61603) required to disrupt the function of an enzyme or protein relative to the absence of the agent (e.g. compound, drug, antagonist, or A61603). A "function increasing amount," as used herein, refers to the amount of an agent (e.g. compound, drug, agonist, or A61603) required to increase the function of an enzyme or protein relative to the absence of the agent (e.g. compound, drug, agonist, or A61603). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is a patient not administered an α1 adrenergic receptor agonist (e.g. A61603). In some embodiments, a control is a biological sample not administered an α1 adrenergic receptor agonist (e.g. A61603). In some embodiments, a control is a cell not administered an α1 adrenergic receptor agonist (e.g. A61603).

"Contacting" is used in accordance with its plain ordinary meaning and refers to the process of allowing at least two distinct species (e.g. agent (e.g. compound, drug, antagonist, agonist, or A61603), chemical compounds including biomolecules, or cells) to become sufficiently proximal to react, interact or physically touch. It should be understood, however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be an agent (e.g. compound, drug, antagonist, agonist, or A61603) as described herein and a receptor (e.g. α1 adrenergic receptor, α1A-AR, α1B-AR, or α1D-AR); or an agent (e.g. compound, drug, antagonist, agonist, or A61603) as described herein and a cardiac cell, heart cell, brain cell, or neuron. In embodiments, a receptor is α1A-AR.

As defined herein, the term "inhibition", "inhibit", "inhibiting" and the like in reference to a target-agent (e.g. compound, drug, antagonist) or protein-inhibitor interaction means negatively affecting (e.g. decreasing) the activity or function of the target or protein relative to the activity or function of the target or protein in the absence of the inhibitor or agent (e.g. compound, drug, antagonist). Thus, inhibition includes, at least in part, partially or totally blocking stimulation, decreasing, preventing, or delaying activation, or inactivating, desensitizing, or down-regulating signal transduction or enzymatic activity. In some embodiments, an "inhibitor" may be a compound that inhibits DNA replication or induces cell death, e.g., by binding, partially or totally blocking stimulation, decrease, prevent, or delay activation, or inactivate, desensitize, or down-regulate signal transduction or enzymatic activity necessary for DNA replication, cell viability, or cell survival.

As defined herein, the term "activation", "activate", "activating", "increase", "increasing" and the like in reference to a target-agent (e.g. compound, drug, agonist) or protein-agonist interaction means positively affecting (e.g. increasing) the activity or function of the target or protein relative to the activity or function of the target or protein in the absence of the activator or agent (e.g. compound, drug, agonist, or A61603). Thus, activation includes, at least in part, partially or totally increasing stimulation, increasing, enabling, or accelerating activation, or activating, sensitizing, or up-regulating signal transduction or enzymatic activity. In some embodiments, an "activator" may be a compound that increases DNA replication or reduces cell death, e.g., by binding, partially or totally increasing stimulation, increase, enable, or accelerate activation, or activate, sensitize, or up-regulate signal transduction or enzymatic activity necessary for DNA replication, cell viability, or cell survival. In embodiments, an activator is A61603.

"Patient" or "subject in need thereof" refers to a living organism suffering from or prone to a condition that can be treated by administration of an agent (e.g. compound, drug, antagonist, agonist, or A61603) or pharmaceutical composition as provided herein. Non-limiting examples include humans, other mammals (e.g. mice, rats, dogs, monkeys, cows, goats, sheep, rabbits) and other non-mammalian animals. In some embodiments, a patient or subject in need thereof is a human with a disease or condition (e.g. heart muscle damage, cardiomyopathy, heart failure, brain damage, or stroke).

"Disease" or "condition" refer to a state of being or health status of a patient or subject capable of being treated with the compounds or methods provided herein. In some embodiments, the disease is a disease related to (e.g. caused by) heart muscle damage (e.g. cardiomyopathy, heart failure) or brain damage (e.g. neurodegenerative diseases, Alzheimer's disease, Parkinson's disease, Huntington's Disease, stroke, aneurysm, cardiovascular disease, cognitive impairment, cognitive deterioration, mild cognitive impairment, cognitive impairment in depressed patients, cognitive deterioration in individuals with Down's syndrome, brain aneurysm, cerebral aneurysm, brain attack, cerebrovascular accident, ischemia, thrombosis, arterial embolism, hemorrhage, transient ischemic attack, embolism, systemic hypoperfusion, venous thrombosis, or reperfusion injury). In some instances, "disease" or "condition" refer to cardiomyopathy, heart failure, or cardiovascular disease or neurodegenerative disease. In some embodiments, the disease is heart muscle damage. In some embodiments, the disease is heart failure. In some embodiments, the disease is cardiomyopathy. In some embodiments, the disease is hypertrophic cardiomyopathy. In some embodiments, the disease is restrictive cardiomyopathy. In some embodiments, the disease is dilated cardiomyopathy. In some embodiments, the disease is dilated congestive cardiomyopathy. In some embodiments, the disease is cardiomyopathy associated with or caused by hypertension, heart valve disease, myocardial ischemia, myocardial inflammation, myocardial infarction, heart failure, pulmonary hypertension, myocardial stunning, myocardial hibernation, cardiac surgery, or coronary intervention. In some embodiments, the disease is heart failure associated with or caused by cardiomyopathy. In some embodiments, the disease is heart failure associated with or caused by cardiomyopathy (e.g. associated with or caused by hypertension, heart valve disease, myocardial ischemia, myocardial inflammation, myocardial infarction, pulmonary hypertension, myocardial stunning, myocardial hibernation, cardiac surgery, or coronary intervention). In some embodiments, the disease is heart failure associated with or caused by idiopathic cardiomyopathy. In some embodiments, the disease is a neurodegenerative disease. In some embodiments, the disease is a cardiovascular disease. In some embodiments, the disease is cardiomyopathy associated with or caused by hypertension, heart valve disease, myocardial ischemia, myocardial inflammation, heart failure, pulmonary hypertension, myocardial stunning, myocardial hibernation, cardiac surgery, or coronary intervention. In some embodiments, the disease is heart failure associated with or caused by cardiomyopathy (e.g. associated with or caused by hypertension, heart valve disease, myocardial ischemia, myocardial inflammation, pulmonary hypertension, myocardial stunning, myocardial hibernation, cardiac surgery, or coronary intervention). In some embodiments, the disease is cardiomyopathy associated with or caused by hypertension, heart valve disease, myocardial inflammation, heart failure, pulmonary hypertension, myocardial stunning, myocardial hibernation, cardiac surgery, or coronary intervention. In some embodiments, the disease is heart failure associated with or caused by cardiomyopathy (e.g. associated with or caused by hypertension, heart valve disease, myocardial inflammation, pulmonary hypertension, myocardial stunning, myocardial hibernation, cardiac surgery, or coronary intervention). In embodiments, the disease is not cardiomyopathy associated with or caused by myocardial infarction. In some embodiments, the disease is not heart failure associated with or caused by cardiomyopathy associated with or caused by myocardial infarction. In embodiments, the disease is not cardiomyopathy associated with or caused by myocardial ischemia. In some embodiments, the disease is not heart failure associated with or caused by cardiomyopathy associated with or caused by myocardial ischemia.

As used herein, the term "neurodegenerative disease" refers to a disease or condition in which the function of a subject's nervous system becomes impaired. Examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

As used herein, the term "cardiovascular disease" refers to a disease or condition affecting the heart or blood vessels. In embodiments, cardiovascular disease includes diseases caused by or exacerbated by atherosclerosis. Exemplary cardiovascular diseases that may be treated with a compound or method provided herein include heart muscle damage, Alcoholic cardiomyopathy, Coronary artery disease, Congenital heart disease, Arrhythmogenic right ventricular cardiomyopathy, Restrictive cardiomyopathy, Noncompaction Cardiomyopathy, diabetes mellitus, hypertension, hyperhomocysteinemia, hypercholesterolemia, Atherosclerosis, Ischemic heart disease, Heart failure, Cor pulmonale, Hypertensive heart disease, Left ventricular hypertrophy, Coronary heart disease, (Congestive) heart failure, Hypertensive cardiomyopathy, Cardiac arrhythmias, Inflammatory heart disease, Endocarditis, Inflammatory cardiomegaly, Myocarditis, Valvular heart disease, stroke, hypertension, heart valve disease, myocardial ischemia, myocardial inflammation, heart failure, pulmonary hypertension, myocardial stunning, myocardial hibernation, cardiomyopathy associated with cardiac surgery, cardiomyopathy associated with coronary intervention or myocardial infarction, cardiomyopathy caused by genetic changes in cardiac proteins, cardiomyopathy associated with genetic mutations in one or more cardiac proteins, cardiomyopathy associated with aberrant expression or function of one or more cardiac proteins. Exemplary cardiovascular diseases that may be treated with a compound or method provided herein include heart muscle damage, Alcoholic cardiomyopathy, Coronary artery disease, Congenital heart disease, Arrhythmogenic right ventricular cardiomyopathy, Restrictive cardiomyopathy, Noncompaction Cardiomyopathy, diabetes mellitus, hypertension, hyperhomocysteinemia, hypercholesterolemia, Atherosclerosis, Ischemic heart disease, Heart failure, Cor pulmonale, Hypertensive heart disease, Left ventricular hypertrophy, Coronary heart disease, (Congestive) heart failure, Hypertensive cardiomyopathy, Cardiac arrhythmias, Inflammatory heart disease, Endocarditis, Inflammatory cardiomegaly, Myocarditis, Valvular heart disease, stroke, hypertension, heart valve disease, myocardial ischemia, myocardial inflammation, heart failure, pulmonary hypertension, myocardial stunning, myocardial hibernation, cardiomyopathy associated with cardiac surgery, cardiomyopathy associated with coronary intervention, cardiomyopathy caused by genetic changes in cardiac proteins, cardiomyopathy associated with genetic mutations in one or more cardiac proteins, cardiomyopathy associated with aberrant expression or function of one or more cardiac proteins. Exemplary cardiovascular diseases that may be treated with a compound or method provided herein include heart muscle damage, Alcoholic cardiomyopathy, Coronary artery disease, Congenital heart disease, Arrhythmogenic right ventricular cardiomyopathy, Restrictive cardiomyopathy, Noncompaction Cardiomyopathy, diabetes mellitus, hypertension, hyperhomocysteinemia, hypercholesterolemia, Atherosclerosis, Heart failure, Cor pulmonale, Hypertensive heart disease, Left ventricular hypertrophy, Coronary heart disease, (Congestive) heart failure, Hypertensive cardiomyopathy, Cardiac arrhythmias, Inflammatory heart disease, Endocarditis, Inflammatory cardiomegaly, Myocarditis, Valvular heart disease, stroke, hypertension, heart valve disease, myocardial inflammation, heart failure, pulmonary hypertension, myocardial stunning, myocardial hibernation, cardiomyopathy associated with cardiac surgery, cardiomyopathy associated with coronary intervention, cardiomyopathy caused by genetic changes in cardiac proteins, cardiomyopathy associated with genetic mutations in one or more cardiac proteins, cardiomyopathy associated with aberrant expression or function of one or more cardiac proteins. In some embodiments, treating a cardiovascular disease includes treating a condition or symptom caused by a cardiovascular disease. A non-limiting example of such a treatment is treating complications due to a myocardial infarction, after the myocardial infarction has occurred. In some embodiments, a cardiovascular disease is cardiomyopathy. In some embodiments, cardiomyopathy is caused by another disease (e.g. a cardiovascular disease) and treatment of cardiomyopathy includes treating the causative disease (e.g. cardiovascular disease) of the cardiomyopathy. In some embodiments, the cardiomyopathy is dilated cardiomyopathy. In some embodiments, the cardiomyopathy is hypertrophic cardiomyopathy. In some embodiments, the cardiomyopathy is hypertrophic, restrictive, or dilated congestive. In embodiments, cardiovascular disease does not include myocardial infarction. In embodiments, treating cardiovascular disease does not include treating a condition or symptom associated with or caused by myocardial infarction (e.g. after the myocardial infarction has occurred). In embodiments, cardiovascular disease does not include myocardial ischemia. In embodiments, treating cardiovascular disease does not include treating a condition or symptom associated with or caused by myocardial ischemia (e.g. after the myocardial ischemia has occurred). In embodiments, cardiovascular disease does not include ischemic heart disease.

As used herein, the term "disease-related cells" means cells that are associated with a disease or condition, which include but are not limited to cells that initiate a disease, cells that propogate a disease, cells that cause a disease, cells that cause one or more symptoms of a disease, cells that are a hallmark of a disease; cells that contain a particular protein or mRNA molecule that causes a symptom of the disease. In some embodiments, the disease is cardiomyopathy and disease-related cells include heart muscle cells, cardiac muscle cells, or cardiomyocytes. In some embodiments, the disease is brain damage and the disease-related cells are brain cells or neurons.

The term "expression" refers to a gene that is transcribed or translated at a detectable level. As used herein, expression also encompasses "overexpression," which refers to a gene that is transcribed or translated at a detectably greater level, usually in a disease-related cell, in comparison to a normal cell. Expression can be detected using conventional techniques for detecting protein (e.g., ELISA, Western blotting, flow cytometry, immunofluorescence, immunohistochemistry, etc.) or mRNA (e.g., RT-PCR, PCR, hybridization, etc.).

As used herein, the term "marker" refers to any biochemical marker, serological marker, genetic marker, or other clinical or echographic characteristic that can be used to diagnose or provide a prognosis for a disease (e.g. cardiomyopathy, cardiovascular disease, neurodegenerative disease, brain damage).

The term "sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "biopsy" refers to the process of removing a tissue sample for diagnostic or prognostic evaluation, and to the tissue specimen itself. Any biopsy technique known in the art can be applied to the diagnostic and prognostic methods of the present invention (e.g. brain biopsy, nerve biopsy, meningeal biopsy, muscle biopsy, heart biopsy). The biopsy technique applied will depend on the tissue type to be evaluated (e.g., brain, glia, nerves, heart, muscle, etc.), among other factors. Representative biopsy techniques include, but are not limited to, excisional biopsy, incisional biopsy, needle biopsy, and surgical biopsy. A diagnosis or prognosis made by endoscopy or fluoroscopy can require a "core-needle biopsy", or a "fine-needle aspiration biopsy" which generally obtains a suspension of cells. Biopsy techniques are discussed, for example, in *Harrison's Principles of Internal Medicine*, Kasper, et al., eds., 16th ed., 2005, Chapter 70, and throughout Part V.

As used herein, the term "administering" means oral administration, parenteral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example additional agents (e.g. compounds, drugs, inhibitors, antagonists, agonists) useful in the treatment of cardiomyopathy or brain damage or agents useful in the treatment of one or more other symptoms of a cardiomyopathy associated disease or brain damage associated disease. The agents (e.g. compounds, drugs, agonists, or A61603) of the invention can be administered alone or can be coadministered to the patient. Coadministration is meant to include simultaneous or sequential administration of the agents (e.g. compounds, drugs, agonists, or A61603) individually or in combination (more than one agent (e.g. compound, drug, agonist)). Thus, the preparations can also be combined, when desired, with other active substances (e.g. to reduce metabolic degradation). The compositions of the present invention can be delivered transdermally, by a topical route, formulated as applicator sticks, solutions, suspensions, emulsions, gels, creams, ointments, pastes, jellies, paints, powders, and aerosols.

"Analog" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound. In some embodiments, a reference compound is A61603.

"A61603" refers to N-[1-(4,5-dihydro-1H-imidazol-2-yl)-6-hydroxy-tetralin-5-yl]methanesulfonamide, or any salt form thereof (e.g. N-[5-(4,5-dihydro-1H-imidazol-2-yl)-2-hydroxy-5,6,7,8-tetrahydronaphthalen-1-yl]methanesulphonamide hydrobromide) (see U.S. Pat. Nos. 4,634,705 and 6,323,231, incorporated herein in their entirety), or any isomer thereof. A61603 has been shown to be at least 35-fold more potent at α1A receptors than at α1B or α1D sites (Knepper et al. (1995), J. Pharmacal. Exp. Ther., 274:97-103). A61603 includes any of the polymorphic forms thereof. A61603 has also been shown to be a more potent α1A AR agonist than the non-selective α1AR agonist phenylephrine. A61603 has also been shown to be a more potent α1A AR agonist than the non-selective α1AR agonists phenylephrine, methoxamine, and midodrine. Cirazoline is not as specific, potent, or efficacious as A61603 in stimulating anabolic effects in cells (e.g. cardiac myocytes). A61603 is efficacious in stimulating anabolic effects in cells (e.g. neurons). Cirazoline has not been tested in neurons. A61603 differs from cirazoline in select cellular signaling pathways in model systems (Evans et al. (2011) Mol. Pharmacol. 79:298-307) (e.g. in embodiments A61603 is a stronger stimulator of cAMP accumulation through α1AR than cirazoline). In embodiments, A61603 is N-[1-(4,5-dihydro-1H-imidazol-2-yl)-6-hydroxy-tetralin-5-yl]methanesulfonamide. In embodiments, A61603 is a salt form of N-[1-(4,5-dihydro-1H-imidazol-2-yl)-6-hydroxy-tetralin-5-yl]methanesulfonamide. In embodiments, A61603 is N-[5-(4,5-dihydro-1H-imidazol-2-yl)-2-hydroxy-5,6,7,8-tetrahydronaphthalen-1-yl]methanesulphonamide hydrobromide.

"Blood Pressure" is the pressure of the blood against the walls of the arteries when the heart beats (systolic pressure) and when the heart is at rest (diastolic pressure). In some embodiments, hypertensive blood pressure may be considered systolic pressure of about 140 mmHg or higher and/or diastolic pressure of about 90 mmHg or higher. In some embodiments, hypertensive blood pressure may be considered systolic pressure of 140 mmHg or higher and/or diastolic pressure of 90 mmHg or higher. "Undesirable blood pressure" or "unhealthy blood pressure" or "high blood pressure" are interchangeable terms and refer to blood pressure levels that are above normal or above healthy blood pressure levels (e.g. hypertensive blood pressure). In some embodiments, high blood pressure is/can be determined by a person of ordinary skill in the art (e.g. doctor, cardiologist, internist, medical doctor). In some embodiments, a high blood pressure is hypertensive blood pressure. In some embodiments, a high blood pressure is 140/90 mmHg or higher. In some embodiments, a high blood pressure or undesirable blood pressure or unhealthy blood pressure is a blood pressure greater than the desirable blood pressure range recommended by the American Heart Association. In some embodiments, a high blood pressure or undesirable blood pressure or unhealthy blood pressure is a blood pressure categorized as hypertensive or pre-hypertensive by the American Heart Association.

In some aspects, the terms "associated" or "associated with" is used herein to describe a first disease in relation to a medical event, a biological compound or a second disease (e.g. a protein associated disease, a cardiomyopathy associated with another disease, brain damage associated with another disease (e.g. stroke, aneurysm, traumatic brain injury)). Where used to describe a first disease in relation to such a medical event, a biological compound or a second disease, the terms "associated" or "associated with" means that the first disease (e.g. cardiomyopathy, brain damage) results from, is correlated with, is caused by, or is a symptom of the medical event, biological compound or a second disease. For example, cardiomyopathy associated with hypertension may be a cardiomyopathy that results (entirely or partially) from hypertension or cardiomyopathy wherein a particular symptom of the disease is caused (entirely or partially) by hypertension. For example, heart failure associated with heart damage (heart muscle damage) may be heart failure that results (entirely or partially) from heart damage (e.g. heart muscle damage) wherein a particular symptom of the disease is caused (entirely or partially) by heart damage (e.g. heart muscle damage). For example, heart failure associated with cardiomyopathy may be heart failure that results (entirely or partially) from cardiomyopathy wherein a particular symptom of the disease is caused (entirely or partially) by cardiomyopathy. As used herein, what is described as being associated with a disease, if a causative agent, could be a target for treatment of the disease. For example, heart failure associated with cardiomyopathy or a cardiomyopathy associated heart failure, may be treated with A61603, in the instance where cardiomyopathy causes the heart failure. For example, cardiomyopathy associated with hypertension may be cardiomyopathy that a subject with hypertension is at higher risk of developing as compared to a subject without hypertension. In some embodiments, where the first disease is "associated" or "associated with" the medical event, biological compound or a second disease, the first disease (or symptom thereof) is caused by the medical event, biological compound or a second disease.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

Cardiomyopathy is a disease of the heart muscle. This form of heart disease is often distinctive, both in general symptoms and in patterns of blood flow, to allow a diagnosis to be made. Increasing recognition of this disease, along with improved diagnostic techniques, has shown that cardiomyopathy is the major cause of heart failure, which has high morbidity and mortality. Cardiomyopathy can result from a variety of structural or functional abnormalities of the ventricular myocardium. There are three clinical classifications of cardiomyopathy: hypertrophic, restrictive, and dilated congestive. Dilated congestive cardiomyopathy is a disorder of myocardial function where impaired systolic function and ventricular dilation occur, classified as ischemic or non-ischemic (toxic, genetic, idiopathic, etc). Restrictive cardiomyopathy is a rare form that occurs as a consequence of the ventricular walls becoming rigid so that the chambers are unable to fill adequately, caused for example by infiltration with amyloid or some other foreign material. Hypertrophic cardiomyopathy is characterized by ventricular hypertrophy and may be congenital or acquired, commonly caused by hypertension. The prognosis for all three types of disease is guarded at best and often poor. Current treatment of cardiomyopathy involves beta-blockers, angiotensin converting enzyme inhibitors, use of anti-coagulants, and cardiac transplantation. When cardiomyopathy is sufficiently advanced, it causes congestive heart failure, with physiological symptoms including breathlessness with exertion or even at rest, swelling of the legs, ankles and feet, bloating (distention) of the abdomen with fluid, fatigue, irregular heartbeats, and dizziness, lightheadedness and fainting.

The α1 adrenergic receptors (α1-ARs) are important mediators of sympathetic nervous system responses, particularly those involved in cardiovascular homeostasis, such as arteriolar smooth muscle constriction and cardiac contraction. In addition, α1-ARs have more recently been implicated in cardiac hypertrophy, cardio-protection, and in ischemic preconditioning. α1-ARs are activated by the catecholamines, norepinephrine and epinephrine.

The α1 adrenergic receptors are members of the superfamily of G protein-coupled receptors and mediate effects related to the regulation of cellular growth and function (Shibata et al. 2003, J. Bioi. Chem. 278:672-678). α1-ARs consist of three subtypes: α1 A-, α1 B-, and α1 D-ARs Graham et al., 1996. Circ. Res. 78:737-749). The three different α1-AR subtypes are expressed in different tissues and various cell types. As a result, studies on the physiological effects mediated by each of the α1-ARs in individual tissues are complicated by the co-existence of multiple α1-AR subtypes (Minneman et al. 1994, Mol. Pharmacal. 46:929-936; Minneman and Esbenshade, 1994. Annu Rev. Pharmacal. Toxicol., 34:117-133; Weinberg eta!, 1994; Biochem. Bio-phys Res. Commun. 201: 1296-1304; Esbenshade et al. 1995; Mol. Pharmacal. 47:977-985; Shibata et al. 1995; Mol. Pharmacal. 48:250-258). Alpha-1-adrenergic receptor agonists are shown herein to be useful in the treatment and prevention of heart and brain diseases. Furthermore, alpha-1-adrenergic receptor agonists (e.g. A61603) are notable for increasing beneficial processes at both functional levels, for example cardiac contraction, and at trophic/protective levels, for example preventing cell death and repairing injury. In some embodiments, the present invention includes the use of alpha-1-adrenergic agonists at doses that are below those that have an effect on smooth muscle contraction.

II. Methods of Treatment

In a first aspect is provided a method of treating or preventing cardiomyopathy in a patient in need of such treatment, the method including administering a therapeutically or prophylactically effective amount of A61603, or an analog, pharmaceutically acceptable salt, or prodrug thereof.

In some embodiments of the method, the cardiomyopathy is dilated cardiomyopathy. In some embodiments of the method, the cardiomyopathy is hypertrophic cardiomyopathy. In some embodiments of the method, the cardiomyopathy is associated with hypertension, heart valve disease, myocardial ischemia, myocardial inflammation, myocardial infarction, heart failure, pulmonary hypertension, myocardial stunning, myocardial hibernation, cardiac surgery, or coronary intervention. In some embodiments, the method includes treating the cardiomyopathy. In some embodiments, the method includes preventing the cardiomyopathy. In some embodiments, the method does not include cardiomyopathy associated with anthracycline treatment. In some embodiments, the method does not include cardiomyopathy associated with doxorubicin treatment. In some embodiments, the method does not include cardiomyopathy associated with chemotherapy treatment. In some embodiments of the method, the cardiomyopathy is idiopathic cardiomyopathy. In some embodiments, the method does not include cardiomyopathy associated with myocardial infarction. In some embodiments of the method, the cardiomyopathy is associated with hypertension, heart valve disease, myocardial ischemia, myocardial inflammation, heart failure, pulmonary hypertension, myocardial stunning, myocardial hibernation, cardiac surgery, or coronary intervention. In some embodiments, the method does not include cardiomyopathy associated with myocardial ischemia. In some embodiments of the method, the cardiomyopathy is associated with hypertension, heart valve disease, myocardial inflammation, heart failure, pulmonary hypertension, myocardial stunning, myocardial hibernation, cardiac surgery, or coronary intervention. In embodiments, the method does not include treating or preventing cardiomyopathy in a patient undergoing treatment with an anthracycline (e.g. doxorubicin, daunorubicin, epirubicin, idarubicin, Adriamycin, or valrubicin).

In a second aspect is provided a method of treating or preventing brain damage in a patient in need of such treatment, the method including administering a therapeutically or prophylactically effective amount of A61603, or an analog, pharmaceutically acceptable salt, or prodrug thereof.

In some embodiments of the method, the brain damage is associated with stroke, ischemia, neurodegenerative disease, or traumatic brain injury. In some embodiments, the method includes treating the brain damage. In some embodiments, the method includes preventing the brain damage.

In a third aspect is provided a method of improving one or more cognitive capabilities in a patient in need of such treatment, the method including administering an effective amount of A61603, or an analog, pharmaceutically acceptable salt, or prodrug thereof.

In some embodiments of the method, the one more cognitive capabilities are selected from the group consisting of learning and memory.

In a fourth aspect is provided a method of treating or preventing heart failure in a patient in need of such treatment, the method including administering a therapeutically or prophylactically effective amount of A61603, or an analog, pharmaceutically acceptable salt, or prodrug thereof. In some embodiments, the method includes improving (e.g. increasing) heart contraction.

In a fifth aspect is provided a method of improving heart contraction in a patient in need of such treatment, the method including administering a therapeutically effective amount of A61603, or an analog, pharmaceutically acceptable salt, or prodrug thereof. In some embodiments, improving heart contraction treats heart failure. In embodiments, improving heart contraction includes improving the volume of the heart contraction, improving strength of the heart contraction, or improving length of the contraction.

In some embodiments of the methods, the patient's blood pressure does not increase as a result of the administration. In some embodiments of the methods, the patient's blood pressure increases by an amount equal to or less than 50, 40, 30, 20, 10, 9, 8, 7, 6, 5, 4, 3, 2, or 1 mmHg as a result of the administration. In some embodiments of the methods, the blood pressure that increases or doesn't increase following administration of A61603 is systolic blood pressure. In some embodiments of the methods, the blood pressure that increases or doesn't increase following administration of A61603 is diastolic blood pressure. In some embodiments of the methods, the patient's blood pressure does not become hypertensive blood pressure from normal blood pressure as a result of the administration. In some embodiments of the methods, the patient's systolic blood pressure does not become hypertensive blood pressure from normal blood pressure as a result of the administration. In some embodiments of the methods, the patient's diastolic blood pressure does not become hypertensive blood pressure from normal blood pressure as a result of the administration. In some embodiments of the methods, the patient's blood pressure does not become prehypertensive blood pressure from normal blood pressure as a result of the administration. In some embodiments of the methods, the patient's systolic blood pressure does not become prehypertensive blood pressure from normal blood pressure as a result of the administration. In some embodiments of the methods, the patient's diastolic blood pressure does not become prehypertensive blood pressure from normal blood pressure as a result of the administration. In some embodiments of the methods, the patient's blood pressure does not become high blood pressure or undesirable blood pressure or unhealthy blood pressure as a result of the administration. In some embodiments of the methods, the patient's blood pressure does not increase to more than 140/90 mmHg as a result of the administration.

In some embodiments of the methods, the effective amount is between about 0.0001 and 10000, 0.001 and 1000, 0.01 and 100, 0.1 and 10, 0.005 and 0.1, 0.005 and 0.05, or 0.007 and 0.02 micrograms/kilogram patient weight. In some embodiments of the methods, the effective amount is about 0.01 micrograms/kilogram patient weight. In some embodiments of the methods, the effective amount is 0.01 micrograms/kilogram patient weight. In some embodiments of the methods, the effective amount is the total amount administered to the patient in a day (e.g. between about 0.0001 and 10000, 0.001 and 1000, 0.01 and 100, 0.1 and 10, 0.005 and 0.1, 0.005 and 0.05, or 0.007 and 0.02 micrograms/kilogram patient weight/day or about 0.01 micrograms/kilogram patient weight/day). In some embodiments of the methods, the effective amount of A61603 administered to a patient or subject in need thereof is 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 micrograms A61603/kilograms patient or subject in need thereof/administration. In some embodiments of the methods, the effective amount of A61603 administered to a patient or subject in need thereof is 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 micrograms A61603/kilograms patient or subject in need thereof/day.

In some embodiments of the methods, the effective amount of A61603 is administered to a patient or subject in need thereof once. In some embodiments of the methods, the effective amount of A61603 is administered to a patient or subject in need thereof for one day. In some embodiments of the methods, the effective amount of A61603 is administered to a patient or subject in need thereof for two days. In some embodiments of the methods, the effective amount of A61603 is administered to a patient or subject in need thereof for three days. In some embodiments of the methods, the effective amount of A61603 is administered to a patient or subject in need thereof for four days. In some embodiments of the methods, the effective amount of A61603 is administered to a patient or subject in need thereof for five days. In some embodiments of the methods, the effective amount of A61603 is administered to a patient or subject in need thereof for six days. In some embodiments of the methods, the effective amount of A61603 is administered to a patient or subject in need thereof for seven days. In some embodiments of the methods, the effective amount of A61603 is administered to a patient or subject in need thereof for two weeks. In some embodiments of the methods, the effective amount of A61603 is administered to a patient or subject in need thereof for three weeks. In some embodiments of the methods, the effective amount of A61603 is administered to a patient or subject in need thereof for four weeks. In some embodiments of the methods, the effective amount of A61603 is administered to a patient or subject in need thereof for about one month. In some embodiments of the methods, the effective amount of A61603 is administered to a patient or subject in need thereof for about two months. In some embodiments of the methods, the effective amount of A61603 is administered to a patient or subject in need thereof for about three months. In some embodiments of the methods, the effective amount of A61603 is administered to a patient or subject in need thereof for about four months. In some embodiments of the methods, the effective amount of A61603 is administered to a patient or subject in need thereof for about five months. In some embodiments of the methods, the effective amount of A61603 is administered to a patient or subject in need thereof for about six months. In some embodiments of the methods, the effective amount of A61603 is administered to a patient or subject in need thereof for about 7, 8, 9, 10, 11, or 12 months. In some embodiments of the methods, the effective amount of A61603 is administered to a patient or subject in need thereof for about one, two, three, four, five, six, seven, eight, nine, ten, 11, 12, 13, 14, 15, 16, 17, 18, 19, 20, or more years. In some embodiments of the methods, the effective amount of A61603 is administered to a patient or subject in need thereof for the duration of the disease (e.g. cardiomyopathy, disease associated with cardiomyopathy, neurodegenerative disease, or brain damage). In some embodiments of the methods, the administering is parenteral, intravenous, intraarterial, buccal, sublingual, oral, peroral, transdermal, or nasal.

In some embodiments, the methods include an effective amount of A61603. In some embodiments, the methods include an effective amount of an analog of A61603. In some embodiments, the methods include an effective amount of an isomer of A61603. In some embodiments, the methods include an effective amount of a pharmaceutically acceptable salt of A61603. In some embodiments, the methods include an effective amount of a prodrug of A61603.

Therapeutically effective doses of A61603 for use in a mammal, which have no effect on blood pressure or which result in no significant increase in blood pressure or result in an acceptable increase in blood pressure (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mmHg, or does not change normal blood pressure to prehypertensive or hypertensive blood pressure, or does not cause the blood pressure to become unhealthy blood pressure or high blood pressure or undesirable blood pressure, or does not cause the blood pressure to be greater than 140/90 mmHg), yet prevent the onset or progression of cardiomyopathy, are determined through standard methods in the art. For example, varying doses of A61603 are administered to a patient (e.g suffering from cardiomyopathy or at risk of developing cardiomyopathy or a patient suffering from brain damage or a patient at risk of developing brain damage or a person suffering from or at risk of suffering from cognitive impairment or a patient who would benefit from enhanced cognitive function or capability), followed by monitoring of blood pressure. Assays to determine whether or not A61603 is effective in preventing the onset of cardiomyopathy, or reducing its progression, are known to persons having ordinary skill in the art and include monitoring of fractional shortening, ejection fraction, end-diastolic volume and troponin levels (methods described in Bielecka-Dabrowa et al. 2008, Cardiology J. 278:1-5; Nellessen et al. 2006, Clin. Cardial. 29:219-224). In one embodiment, no increase in blood pressure is observed when the blood pressure is measured 24 hours after treatment, in another embodiment no increase in blood pressure is observed when the blood pressure is measured 48 hours, 72 hours, 1 week or 1 month after treatment. In yet another embodiment, blood pressure, when measured after 48 hours, 72 hours, 1 week, or 1 month, increases less than 10% or less than 15% after treatment with A61603. In some embodiments, blood pressure increases (e.g. by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mmHg) following administration of a therapeutically effective or prophylactically effective amount of A61603. In some embodiments, blood pressure increases following administration of a therapeutically effective or prophylactically effective amount of A61603 but does not change from normal to prehypertensive or from normal to hypertensive or from prehypertensive to hypertensive blood pressure. In some embodiments, blood pressure increases following administration of a therapeutically effective or prophylactically effective amount of A61603 but does not become an undesirable blood pressure, high blood pressure, or unhealthy blood pressure. In some embodiments, blood pressure increases following administration of a therapeutically effective or prophylactically effective amount of A61603 but does not become greater than 140/90 mmHg.

In one embodiment, administration of a dose of A61603 at an amount which does not increase blood pressure prevents the onset or progression of cardiomyopathy or brain damage in a patient suffering from or at risk of cardiomyopathy or brain damage or who would benefit from increased cognitive capabilities (e.g. learning or memory). In one embodiment, administration of a dose of A61603 at an amount which does not increase blood pressure from normal to hypertensive prevents the onset or progression of cardiomyopathy or brain damage in a patient suffering from or at risk of cardiomyopathy or brain damage or who would benefit from increased cognitive capabilities (e.g. learning or memory). In one embodiment, administration of a dose of A61603 at an amount which does not increase blood pressure to high blood pressure, unhealthy blood pressure, or undesirable blood pressure, prevents the onset or progression of cardiomyopathy or brain damage in a patient suffering from or at risk of cardiomyopathy or brain damage or who would benefit from increased cognitive capabilities (e.g. learning or memory). In one embodiment, administration of a dose of A61603 at an amount which does not increase blood pressure to greater than 140/90 mmHg, prevents the onset or progression of cardiomyopathy or brain damage in a patient suffering from or at risk of cardiomyopathy or brain damage or who would benefit from increased cognitive capabilities (e.g. learning or memory).

Progression of cardiomyopathy may be monitored in part by measuring levels of serum biomarkers, such as creatine kinase, troponin, ST2 (e.g. soluble ST2), GDF-15, or brain natriuretic peptide (BNP).

Progression of cardiomyopathy may be assessed in part by measuring fractional shortening (FS) or ejection fraction (EF). FS is used to measure left ventricle performance by measuring the change in the diameter of the left ventricle between the contracted and relaxed state on M-mode tracings and calculating the ratio according to the formula: [(LV end-diastolic diameter-LV end-systolic diameter)/LV end-diastolic diameter)]×100. EF is calculated from left ventricular volumes determined by 2-dimensional echo, as [(LV end-diastolic volume-LV end-systolic volume)/LV end-diastolic volume)]×100. A decrease in FS or EF is indicative of heart damage. In one embodiment, a therapeutically effective amount of A61603 is administered to a subject suffering from or at risk of cardiomyopathy, wherein the A61603 prevents more than 5-30% (e.g. more than 5, 6, 7, 8, 9, 10, 11, 12, 13, 14, 15, 16, 17, 18, 19, 20, 21, 22, 23, 24, 25, 26, 27, 28, 29, or 30%) reduction in the FS or EF as compared to a subject suffering from or at risk of cardiomyopathy not administered A61603. In another embodiment, administration of A61603 to a subject suffering from or at risk of cardiomyopathy prevents more than 5% reduction in the FS or EF as compared to a subject suffering from or at risk of cardiomyopathy not administered A61603.

In one embodiment, a therapeutically effective amount of A61603 is administered to a subject suffering from or at risk of cardiomyopathy, wherein the A61603 prevents more than 5-30% (e.g. more than 5, 6, 7, 8, 9, 10, 11, 12, 13, 14, 15, 16, 17, 18, 19, 20, 21, 22, 23, 24, 25, 26, 27, 28, 29, or 30%) increase in the end-diastolic volume as compared to a subject suffering from or at risk of cardiomyopathy not administered A61603. In another embodiment, administration of A61603 to a subject suffering from or at risk of cardiomyopathy prevents more than 5% increase in the end-diastolic volume as compared to a subject suffering from or at risk of cardiomyopathy not administered A61603.

In some embodiments, cardiomyopathy is detected by a method selected from the group consisting of X-ray (e.g. chest), echocardiogram, electrocardiogram, cardiac catheterization, cardiac biopsy, computerized tomography, and magnetic resonance imaging. In some embodiments, brain damage is detected by a method selected from the group consisting of magnetic resonance imaging, functional magnetic resonance imaging, positron emission tomography, single photon emission computed tomography, computerized axial tomography, computerized tomography, electroencephalography, and magnetoencephalography.

It is well known that creatine kinase (CK) or troponin are released from myocytes when myocyte necrosis occurs. Accordingly, measuring levels of CK or troponin in the serum may be done to assess the onset and progression of cardiomyopathy in a subject. Measuring serum CK levels is done using methods known to those of ordinary skill in the art, for example, by a coupled reaction of glucokinase and glucose-6-phosphate dehydrogenase using a diagnostic kit. In one embodiment, a therapeutically effective amount of A61603 is administered to a subject suffering from or at risk of cardiomyopathy, wherein the A61603 reduces the level of CK in the serum of the subject as compared to CK levels found in the serum of a subject suffering from or at risk of cardiomyopathy not administered A61603. In some embodiments, a therapeutically effective amount of A61603 is administered to a subject suffering from or at risk of cardiomyopathy, wherein the A61603 reduces the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy not administered A61603. In one embodiment, a therapeutically effective amount of A61603 is administered to a subject suffering from or at risk of cardiomyopathy, wherein the A61603 increases the level GDF-15 in the serum of the subject as compared to GDF-15 levels found in the serum of a subject suffering from or at risk of cardiomyopathy not administered A61603. In some embodiments, a therapeutically effective amount of A61603 is administered to a subject suffering from or at risk of cardiomyopathy, wherein the A61603 does not modulate the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy not administered A61603. In some embodiments, a therapeutically effective amount of A61603 is administered to a subject suffering from or at risk of cardiomyopathy, wherein the A61603 improves the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy not administered A61603. In some embodiments, improvement of the level of BNP, GDF-15, or ST2 (e.g. soluble ST2) in the serum of the subject is lowering of the level. In some embodiments, improvement of the level of BNP, GDF-15, or ST2 (e.g. soluble ST2) in the serum of the subject is increasing the level. In some embodiments, improvement of the level of BNP, GDF-15, or ST2 (e.g. soluble ST2) in the serum of the subject is as recommended by the American Heart Association. In some embodiments, determining what constitutes an improvement of the level of BNP, GDF-15, or ST2 (e.g. soluble ST2) in the serum of the subject is well within the skill of a person of ordinary skill in the art (e.g. doctor, cardiologist, internist).

Another indicator of cardiomyopathy is increased cardiomyocyte apoptosis. Cardiomyocyte apoptosis may be measured by methods known in the art, including for example by MRI, optionally including probes such as Annexin V (ANX), superparamagnetic iron oxide (SPIO), ANX conjugated to SPIO (ANX-SPIO), ANX conjugated to other detectable moieties, other phosphatidylserine binding detectable moieties, or other MRI probes known in the art (see Dash, R. et al. *Magn. Reson. Med.* 2011; 66:1152-1162 incorporated herein in its entirety). Cardiomyopathy is also accompanied by an increase in fibrosis of the cardiac tissue. Fibrosis may be measured using Sirius Red staining, a method well known to skilled artisans. In one embodiment, a therapeutically effective amount of A61603 is administered to a subject suffering from or at risk of cardiomyopathy, wherein the A61603 reduces the area of fibrosis in the heart as compared to a subject suffering from or at risk of cardiomyopathy not administered A61603.

In one embodiment, the method prevents a decrease in fractional shortening in the subject by more than 5% to 30% (e.g. more than 5, 6, 7, 8, 9, 10, 11, 12, 13, 14, 15, 16, 17, 18, 19, 20, 21, 22, 23, 24, 25, 26, 27, 28, 29, or 30%) as compared to fractional shortening in a subject suffering from or at risk of cardiomyopathy not administered A61603.

In one embodiment, the method prevents an increase in the amount of creatine kinase or troponin in the serum of the subject by more than 2-fold, 4-fold, or 5-fold as compared to the amount of creatine kinase or troponin in the serum of the subject suffering from or at risk of cardiomyopathy not administered A61603. In one embodiment, the method prevents an increase in the amount of ST2 (interleukin 1 receptor-like 1) (e.g. soluble ST2), GDF-15 (growth differentiation factor 15), or BNP (brain natriuretic peptide) as compared to the amount of ST2, GDF-15, or BNP in the serum of the subject suffering from or at risk of cardiomyopathy not administered A61603. In one embodiment, the method increases the amount of ST2 (interleukin 1 receptor-like 1) (e.g. soluble ST2), GDF-15 (growth differentiation factor 15), or BNP (brain natriuretic peptide) as compared to the amount ST2, GDF-15, or BNP in the serum of the subject suffering from or at risk of cardiomyopathy not administered A61603. In one embodiment, the method decreases the amount of ST2 (interleukin 1 receptor-like 1) (e.g. soluble ST2), GDF-15 (growth differentiation factor 15), or BNP (brain natriuretic peptide) as compared to the amount ST2, GDF-15, or BNP in the serum of the subject suffering from or at risk of cardiomyopathy not administered A61603.

In one embodiment, the method prevents an increase in the percentage of cardiac fibrosis area by more than 1% to 20% (e.g. by more than 1, 2, 3, 4, 5, 6, 7, 8, 9, 10, 11, 12, 13, 14, 15, 16, 17, 18, 19, or 20%) in the heart of the subject suffering from or at risk of cardiomyopathy not administered A61603.

In some embodiments, the methods include improving (e.g. increasing) heart contraction in a patient. In some embodiments, the methods include preventing heart muscle cells from dying. In some embodiments, the methods include stimulating repair of heart muscle. In some embodiments, the methods include stimulating anabolic processes or function in cells (e.g. cardiac muscle cells) or tissue (e.g. cardiac tissue).

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intracranially, intracardiac administration, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. α1 adrenergic receptor), and/or reducing, eliminating, or slowing the progression of disease symptoms (e.g. cardiomyopathy, brain damage). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art. As is well known in the art, therapeutically effective amounts for use in humans can also be determined from animal models. For example, a dose for humans can be formulated to achieve a concentration that has been found to be effective in animals (e.g. 10 ng/kg/day in an animal model can be translated to an amount in humans by one of skill). The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As non-limiting examples, the compositions, drugs, and compounds described herein can be co-administered with or used in combination with cardiomyopathy agents including, but not limited to beta-adrenergic blockers, angiotensin converting enzyme inhibitors, or aldosterone or angiotensin receptor blockers. As non-limiting examples, the compositions, drugs, and compounds described herein can be co-administered with or used in combination with other agents for treating brain damage. As non-limiting examples, the compositions, drugs, and compounds described herein can be co-administered with or used in combination with other agents useful in improving cognitive function and capabilities. As non-limiting examples, the compositions, drugs, and compounds described herein can be co-administered with or used in combination with other agents useful in increasing the cellular uptake (e.g. uptake by cardiac cells, brain cells, or neurons) of the compositions, drugs, or compounds (e.g. A61603) for treating diseases (e.g. cardiomyopathy, heart muscle damage, brain damage). In some embodiments the cellular uptake is increased by activating a transporter protein in the cell.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged A61603 suspended in diluents, e.g., water, saline, or PEG 400; (b) capsules, sachets, or tablets, each containing a predetermined amount of A61603, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise A61603 in a flavor, e.g., sucrose, as well as pastilles comprising A61603 in an inert base, such as gelatin and glycerin or sucrose and acacia emulsions, gels, and the like, containing, in addition to A61603, carriers known in the art.

The alpha-1 adrenergic receptor agonist of choice (e.g. A61603), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. In some embodiments, aerosol formulations are used to administer an alpha-1 adrenergic receptor agonist of choice (e.g. A61603) to the lungs. In some embodiments, aerosol formulations are used to administer an alpha-1 adrenergic receptor agonist of choice (e.g. A61603) to the brain (e.g. through the nose).

Formulations suitable for parenteral administration, such as, for example, by intraarticular (in the joints), intravenous, intramuscular, intratumoral, intradermal, intraperitoneal, intracranial, intracardiac, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, intracardiac administration, orally, topically, intraperitoneally, intravesically, intracranially, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., A61603. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The compounds described herein can be used in combination with one another, with other active agents known to be useful in treating cardiomyopathy, cardiovascular diseases, neurodegenerative diseases, brain damage, or that are useful in improving cognitive function or capabilities, or with adjunctive agents that may not be effective alone, but may contribute to the efficacy of the active agent.

III. Additional Embodiments

1. A method of treating or preventing cardiomyopathy in a patient in need of such treatment, said method comprising administering a therapeutically or prophylactically effective amount of A61603, or an analog, pharmaceutically acceptable salt, or prodrug thereof.

2. The method of embodiment 1, wherein said cardiomyopathy is dilated cardiomyopathy.

3. The method of embodiment 1, wherein said cardiomyopathy is hypertrophic cardiomyopathy.

4. The method of embodiment 1, wherein said cardiomyopathy is associated with hypertension, heart valve disease, myocardial ischemia, myocardial inflammation, myocardial infarction, heart failure, pulmonary hypertension, myocardial stunning, myocardial hibernation, cardiac surgery, genetic mutation, genetic changes in cardiac proteins, or coronary intervention.

5. The method of embodiment 1, wherein said cardiomyopathy is associated with hypertension, heart valve disease, myocardial inflammation, heart failure, pulmonary hypertension, myocardial stunning, myocardial hibernation, cardiac surgery, genetic mutation, genetic changes in cardiac proteins, or coronary intervention.

6. The method of any one of embodiments 1 to 5, wherein said method comprises treating said cardiomyopathy.

7. The method of any one of embodiments 1 to 5, wherein said method comprises preventing said cardiomyopathy.

8. A method of treating or preventing brain damage in a patient in need of such treatment, said method comprising administering a therapeutically or prophylactically effective amount of A61603, or an analog, pharmaceutically acceptable salt, or prodrug thereof.

9. The method of embodiment 8, wherein said brain damage is associated with stroke, ischemia, neurodegenerative disease, or traumatic brain injury.

10. The method of any one of embodiments 8 to 9, wherein said method comprises treating said brain damage.

11. The method of any one of embodiments 8 to 9, wherein said method comprises preventing said brain damage.

12. A method of improving one or more cognitive capabilities in a patient in need of such treatment, said method comprising administering an effective amount of A61603, or an analog, pharmaceutically acceptable salt, or prodrug thereof.

13. The method of embodiment 12, wherein said one more cognitive capabilities is selected from the group consisting of learning and memory.

14. The method of any one of embodiments 1 to 13, wherein said patient's blood pressure does not increase as a result of said administration.

15. The method of any one of embodiments 1 to 13, wherein said patient's blood pressure increases by an amount equal to or less than 50, 40, 30, 20, 10, 9, 8, 7, 6, 5, 4, 3, 2, or 1 mmHg as a result of said administration.

16. The method of embodiment 15, wherein said blood pressure is systolic blood pressure.

17. The method of any one of embodiments 1 to 13, wherein said effective amount is between about 0.0001 and 10000, 0.001 and 1000, 0.01 and 100, 0.1 and 10, 0.005 and 0.1, 0.005 and 0.05, or 0.007 and 0.02 micrograms/kilogram patient weight.

18. The method of any one of embodiments 1 to 13, wherein said effective amount is about 0.01 micrograms/kilogram patient weight.

19. The method of any one of embodiments 1 to 13, wherein said effective amount is 0.01 micrograms/kilogram patient weight 20. The method of any one of embodiments 17 to 19, wherein said effective amount is the total amount administered to said patient in a day.

21. The method of any one of embodiments 1 to 20, wherein said administering is parenteral, intravenous, intraarterial, buccal, sublingual, oral, peroral, transdermal, or nasal.

IV. Examples

Alpha-1-adrenergic receptor agonists for the prevention and treatment of heart muscle injuries and diseases, and for prevention and treatment of neuronal injuries or diseases. One part of the invention is to use a drug or drugs that activate alpha-1 adrenergic receptors in cardiac muscle cells or other cardiac cells, to treat heart muscle diseases, or to prevent heart muscle disease from occurring. Diseases treated by giving an alpha-1 adrenergic agonist after the disease is present would include, but not be limited to: heart failure; cardiomyopathy from hypertension or valve disease or ischemia or idiopathic; myocardial stunning; myocardial hibernation; myocardial dysfunction post-myocardial infarction; myocardial dysfunction post-cardiac surgery; myocardial dysfunction post-coronary intervention; anthracycline-induced cardiomyopathy; other cancer chemotherapy-induced cardiomyopathy; right ventricle failure from pulmonary hypertension or other causes. Diseases prevented by giving an alpha-1-adrenergic agonist before the disease is present would be the same, with two specific examples being anthracycline-induced cardiomyopathy and preconditioning before coronary intervention or bypass or other invasive procedures. Also described herein is use of a drug or drugs that activate alpha-1 adrenergic receptors on the brain neurons or other brain cells to provide neuroprotection to treat neurological diseases or injuries. Diseases prevented or treated by giving an alpha-1 adrenergic receptor agonist would include, but not be limited to: traumatic brain injury; ischemic brain injury (e.g. stroke); Parkinson's disease; Alzheimer's disease; and other neurodegenerative diseases.

For all cardiac and neurological indications, a drug or drugs would be given to activate alpha-1-adrenergic receptors, receptors that normally are activated by catecholamines such as norepinephrine or epinephrine. The drug might activate all subtypes of alpha-1-adrenergic receptor (there are currently 3 known subtypes), or only one or two of the subtypes, or only a particular active state of the subtype (receptors have multiple active states). The effect of the drug would be to increase post-receptor signaling in the cell, for example the cardiac muscle cell or neuron, and this increased signaling would have beneficial effects in the heart or brain by increasing beneficial anabolic or trophic or metabolic processes, or by stimulating mechanisms that protect from cell injury or death, or by increasing cardiogenesis or neurogenesis. In some embodiments, the drug or compound (e.g. A61603) and/or methods described herein bind to the alpha-1A subtype. Another mechanism of benefit, in addition to the trophic and protective mechanisms described herein above, is to stimulate acute adaptive processes. This includes improving cardiac function by activating contraction, and improving brain function by stimulating learning and memory.

Analysis of Alpha-1A Agonists In Vitro

Figure 2:
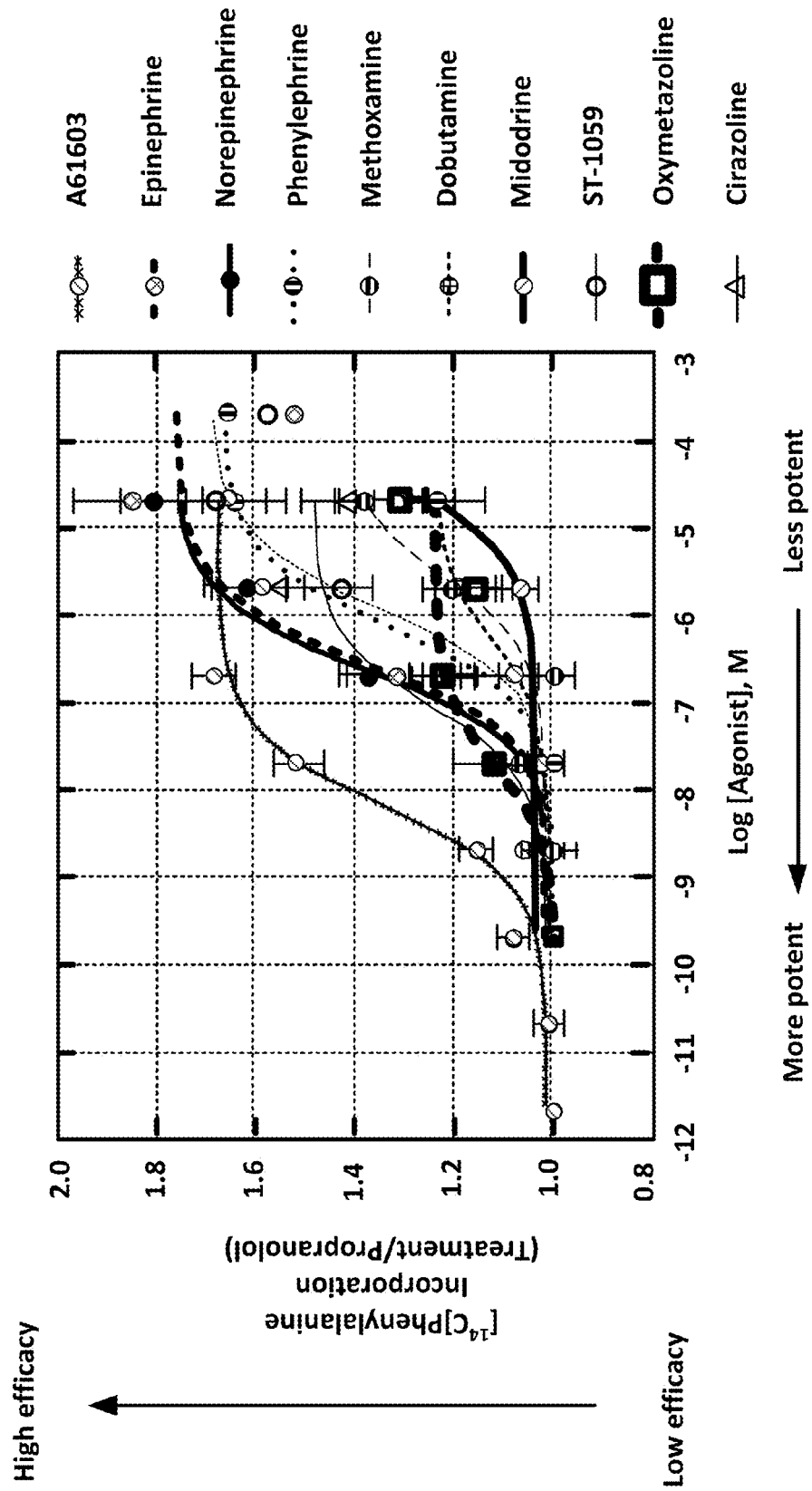
FIG. 2. A61603 is adaptive in neonatal cardiac muscle cells. A61603 activates protein synthesis, an anabolic, adaptive process, with high efficacy and potency, in neonatal rat cardiac muscle cells in vitro.
Figure 3:
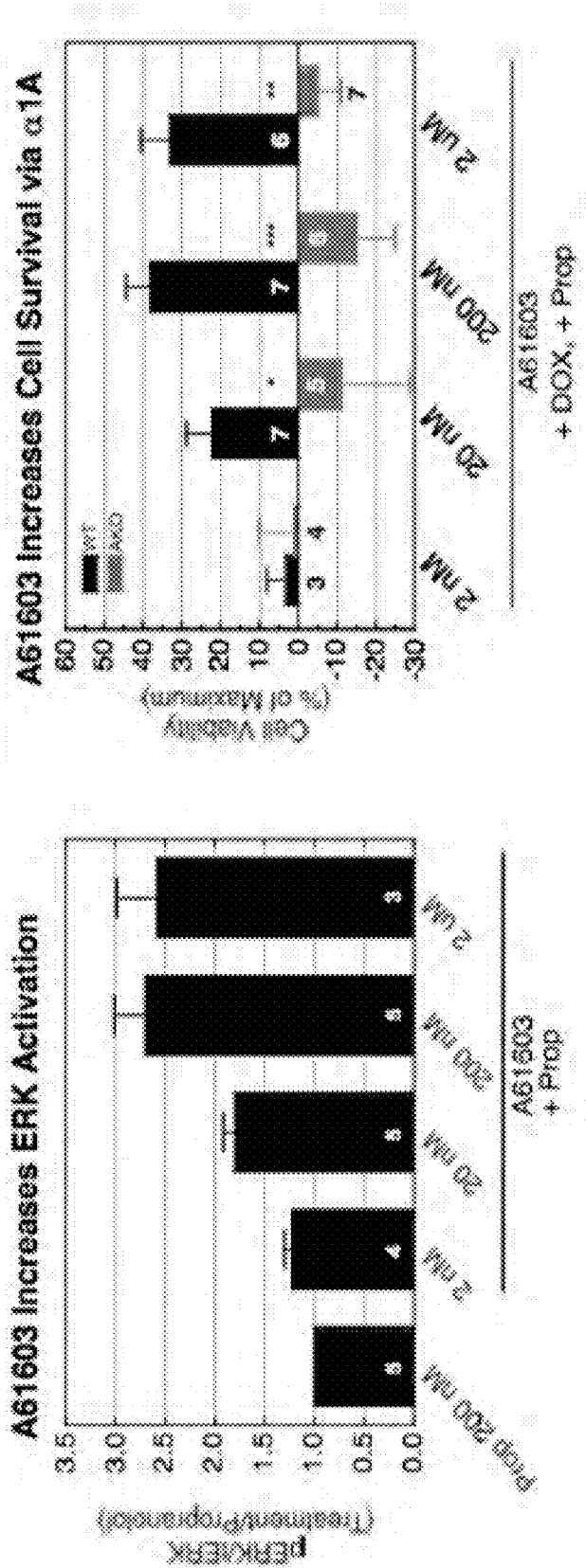
FIG. 3. A61603 protects adult cardiac muscle cells. In adult mouse cardiac muscle cells, A61603 at a low concentration activates ERK (left), and protects against a cardiotoxic cancer drug, (DOX) (right). These effects are not blocked by a beta-blocker, propranolol (Prop), which is current standard of care in heart failure therapy. That is, A61603 effects are additive to those of a beta-blocker. Knockout of the alpha-1A receptor (AKO) eliminates myocyte protection by A61603 (right), showing that the drug does indeed work through the alpha-1A, as expected.

First, experiments in vitro on cardiac cell protective and adaptive effects, with neonatal rat cardiac myocytes and adult mouse cardiac myocytes, showed that the alpha-1A subtype agonist, A61603, was more potent (i.e. worked at a lower dose) and efficacious (i.e. had a larger total effect), than several other alpha-1-agonists (FIG. 1-3).

Determination of Administration Amount and Analysis In Vivo

Figure 4:
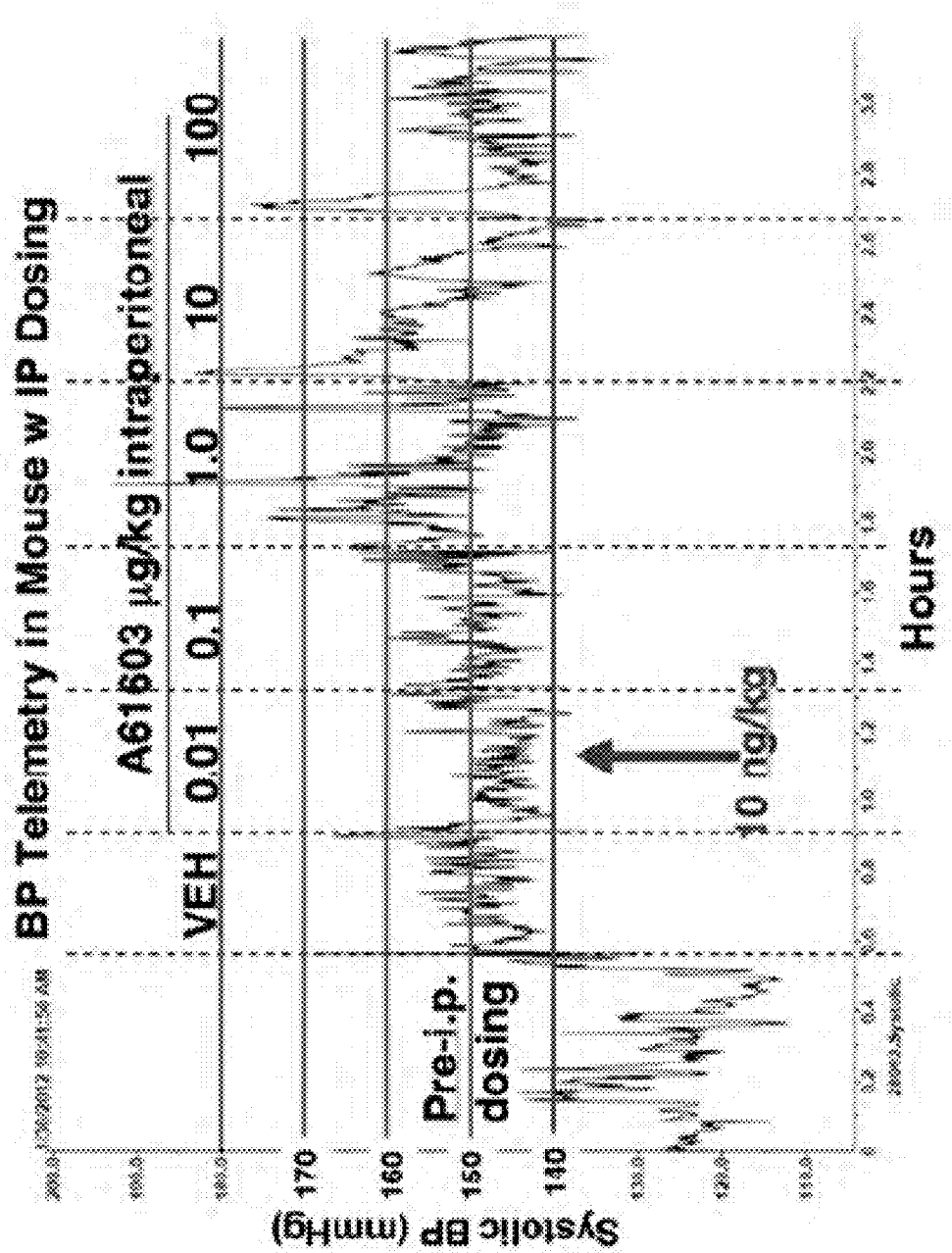
FIG. 4. A61603 at 10 ng/kg does not change BP. A61603 at 10 ng/kg injected acutely intraperitoneal does not increase BP measured by indwelling arterial catheter.
Figure 5:
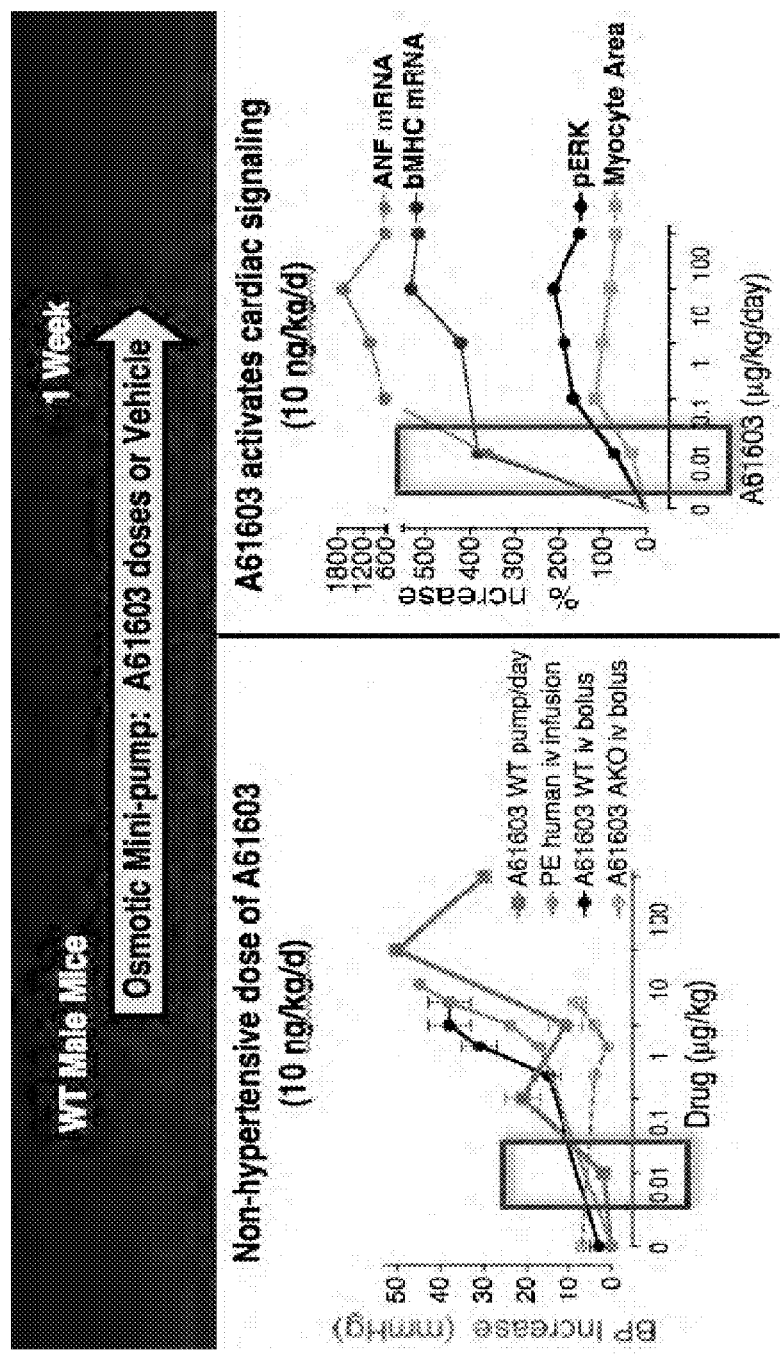
FIG. 5. A61603 activates heart signaling at a BP-neutral dose. A61603 was infused subcutaneously (osmotic minipump) for 1 week in adult mice, and BP was measured daily. There was no change in average BP at the low dose, in agreement with the intravenous (IV) route in another study, and with phenylephrine (PE) given in humans (left side). BP effects of A61603 are absent in the alpha-1A KO (AKO), again showing the selectivity of the drug for that receptor (left). At the end of 1 week, the heart was removed to measure ERK activation, and increases in heart mRNAs and area (size), reflecting protective (ERK) adaptive (mRNAs, area) effects on heart muscle cells. A61603 at the low dose of 10 ng/kg/d increased these endpoints.

Next, experiments in vivo in the adult mouse defined a dose of A61603 that did not change blood pressure (BP), but at the same time did act on alpha-1A receptors in the heart to activate protective and adaptive molecular signaling (FIG. 4-5). The classic effect of alpha-1-agonists is to increase BP by stimulating smooth muscle cells to contract. It could be a disadvantage in heart failure (HF) therapy to increase BP excessively. On the other hand, all current recommended drugs in HF reduce BP, and a drug that increased BP slightly might have a strong therapeutic advantage. The dose of A61603 that does not change BP in the mouse was identified in 2 ways, by acute injection into the peritoneum and measuring BP by an indwelling catheter with a remote telemeter (FIG. 4), and by chronic subcutaneous infusion of drug and measuring BP by a cuff around the tail (FIG. 5). The foregoing experiments provided the rationale to test treatment with A61603 at 10 ng/kg/d in a mouse model of cardiomyopathy and HF.

Figure 6:
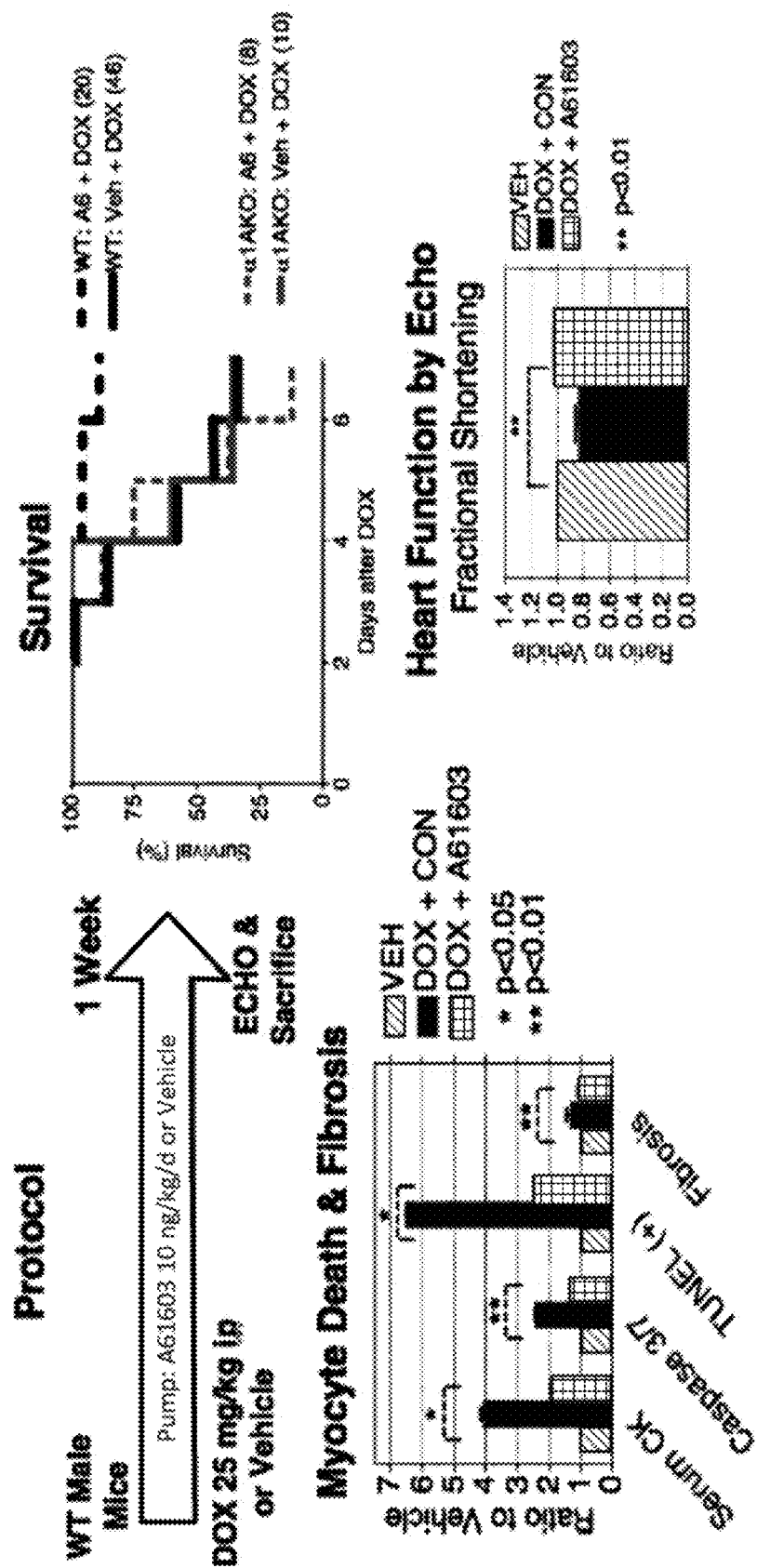
FIG. 6. A61603 prevents doxorubicin cardiomyopathy. DOX was given to adult mice in a single intraperitoneal dose of 25 mg/kg. A61603 was infused subcutaneously (osmotic minipump) for 1 week (top left). We monitored mouse survival over the week, and at the end of 1 week measured heart cell damage and function. A61603 markedly improved survival after DOX, as compared with mice given DOX and treated with vehicle, and this protective effect required the alpha-1A receptor, as it was lost in the alpha-1A knockout (KO) (top right). In surviving mice, A61603 treatment improved heart function measured by echocardiography (fractional shortening, an index of contraction) (bottom right). A61603 treatment also improved indices of myocardial fibrosis, cell death by apoptosis (caspase 3/7 activity and TUNEL staining), and cell death by necrosis (serum CK, or creatine kinase) (bottom left).

In summary, the alpha-1A agonist A61603 is protective and adaptive in cardiac muscle cells in vitro and in vivo. These effects require the alpha-1A receptor (i.e. they are not off-target effects), and occur at a dose that does not change BP. A61603 protects against mortality and cardiomyopathy, by preventing cell death and fibrosis. We chose a model of cardiomyopathy caused by a cancer drug, the anthracycline doxorubicin (DOX). Cancer drug cardiotoxicity is a common and growing problem. We used the same protocol that tested A61603 BP and signaling effects (FIG. 5). Results showed that A61603 treatment prevented the cardiomyopathy, as measured by mouse survival, heart function, heart fibrosis, and heart cell death due to apoptosis or necrosis (FIG. 6).

Pressure-Overload Heart Failure

Figure 7:
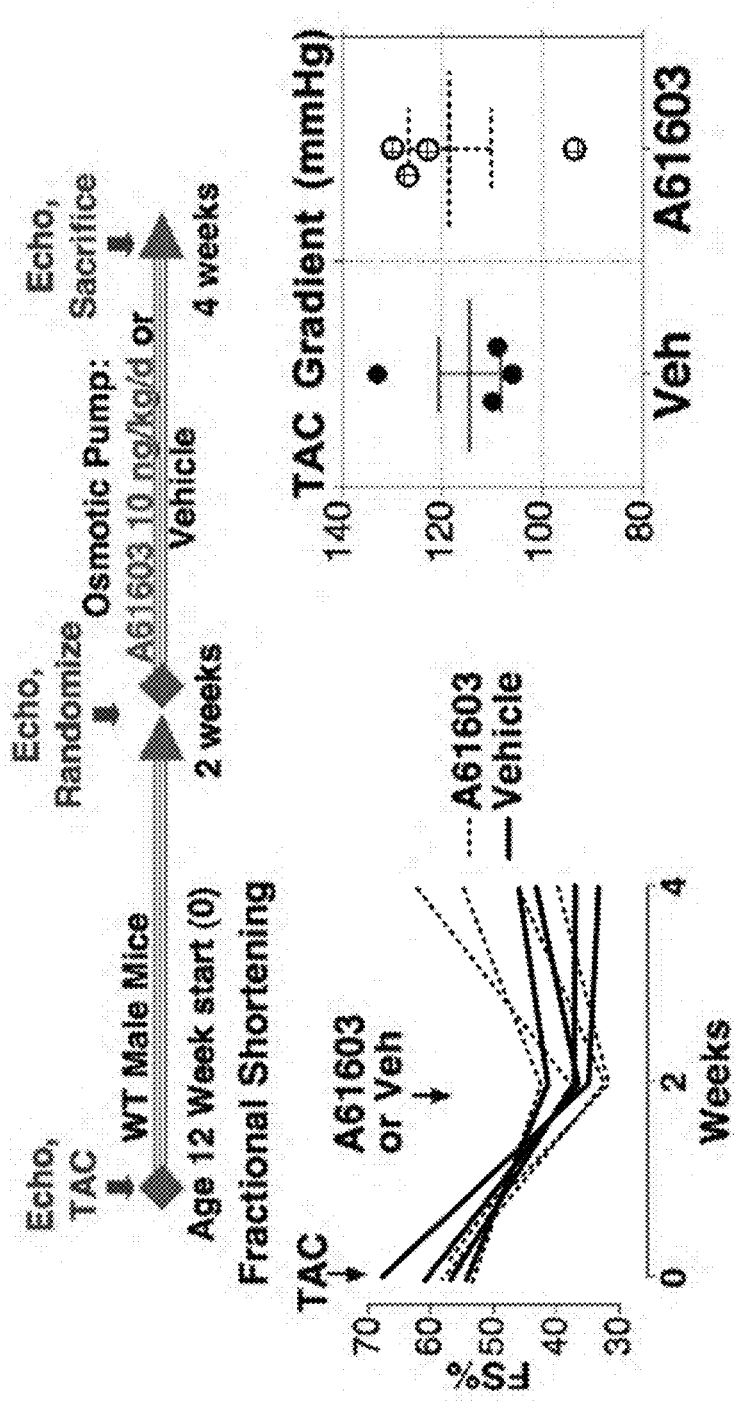
FIG. 7. A61603 rescues pressure overload cardiomyopathy. Mice had echo 2 weeks after TAC, at which time they were randomized to treatment with A61603, at the same low dose, or vehicle. Fractional shortening, an index of cardiac function, was depressed by TAC, and improved with A61603, but not with vehicle. The degree of overload (the gradient) was the same in both groups, ruling out any spurious improvement by A61603.
Figure 8:
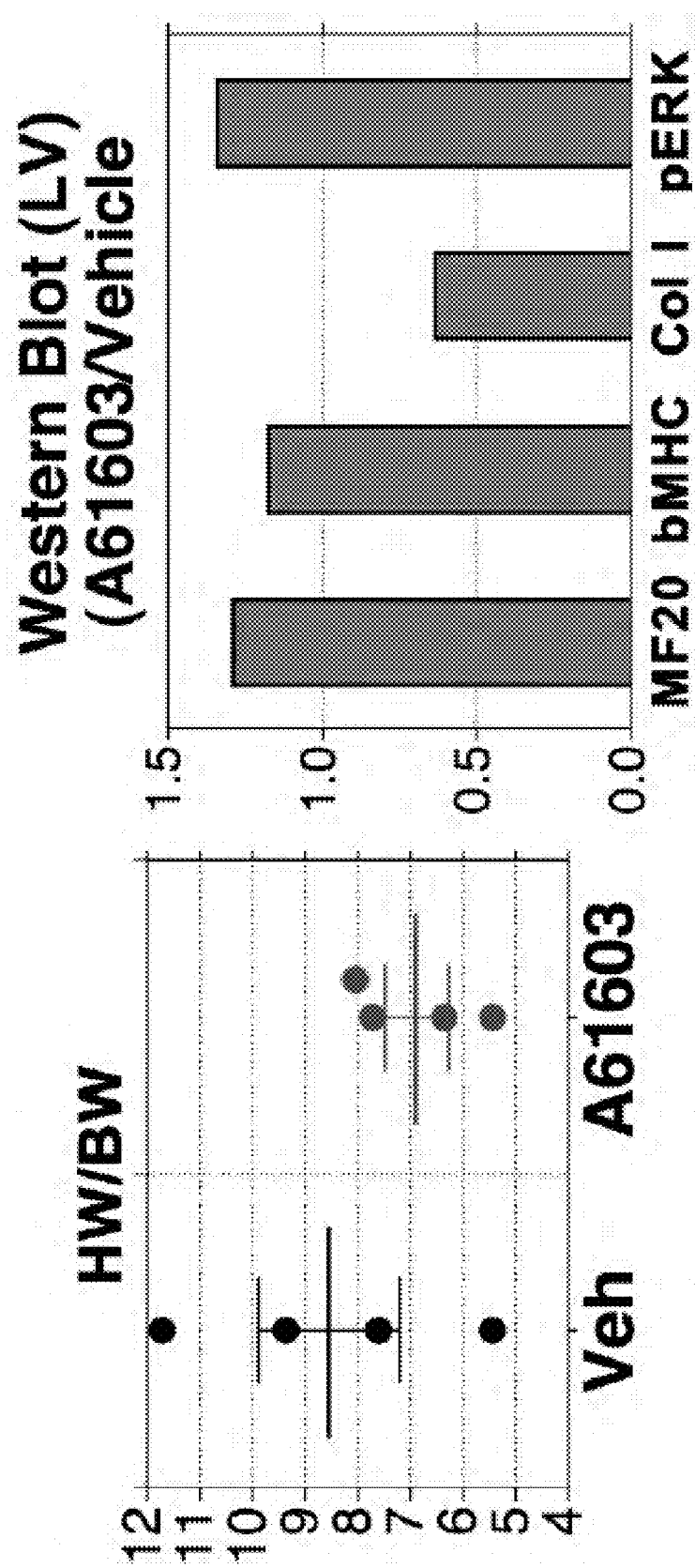
FIG. 8. A61603 in pressure overload cardiomyopathy improves growth and protection, and reduces fibrosis. Hearts of mice treated with A61603 had less abnormal enlargement (heart weight normalized to body weight, or HW/BW, left), less collagen fibrosis (Col I, right), more adaptive proteins (myosin or MF20 and beta-myosin or bMHC), and higher protection (ERK, right).

Studies in mice looking at alpha-1 agonist therapy, using A61603, in a model of heart failure due to pressure overload (transverse aortic constriction model). A model of pressure overload was tested for 2 reasons: (1) test generality of A61603 effects in different types of cardiomyopathy; and (2) test treatment (rescue), rather than prevention, i.e. A61603 given at an interval of time after injury, when cardiomyopathy was already manifest. We used an adult mouse model of transverse aortic constriction (TAC), with the aorta surgically narrowed, so that the heart had to pump against an increased pressure (pressure overload). This model simulates multiple aspects of cardiac disease, and shows utility of alpha-1 adrenergic agonists in the treatment of cardiomyopathy associated with hypertension, valve disease, acute ischemia, and inflammation among other diseases and conditions. A61603 treatment rescued the cardiomyopathy, as measured by heart function (FIG. 7). A61603 in the TAC model resulted in less abnormal heart enlargement, reduced heart fibrosis, increased heart protection (increased ERK), and increased myocyte adaptive proteins (the myosin proteins responsible for contraction) (FIG. 8). Thus improvement in function caused by A61603 was again due to direct effects on cardiac muscle cells. The alpha-1A agonist A61603 at a low dose rescues (e.g. treats) cardiomyopathy due to pressure overload, an injury that simulates several types of cardiac disease, and the mechanism is improvement of cardiac myocytes.

Cardiomyopathy and/or Heart Failure Following Myocardial Infarction (Heart Attack)

Figure 9:
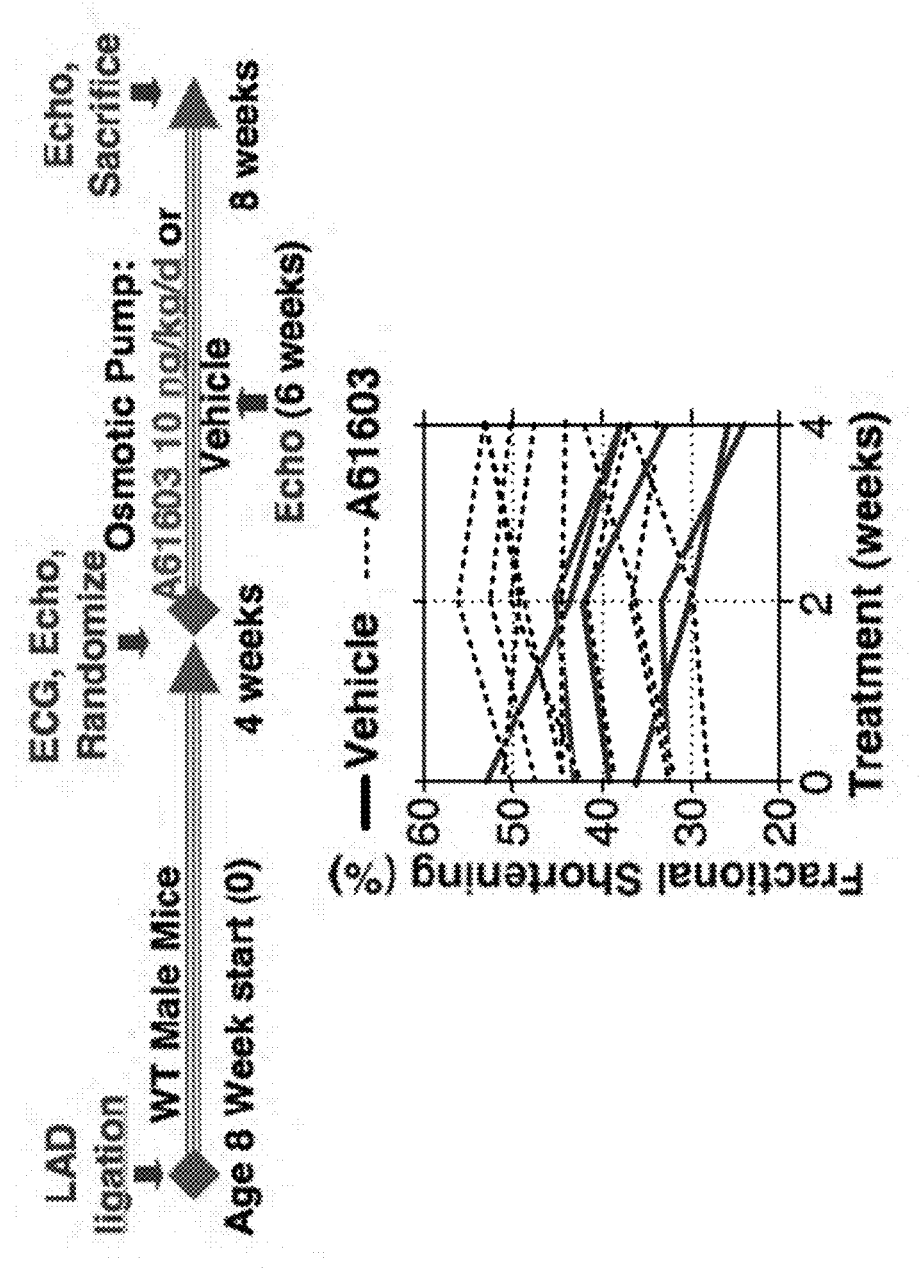
FIG. 9. A61603 rescues ischemic, post-myocardial infarction (MI) cardiomyopathy. Mice had echo 4 weeks after LAD ligation (MI), at which time they were randomized to treatment with A61603, at the same low dose, or vehicle. Fractional shortening, an index of cardiac function, stayed the same or improved with A61603, but continued to deteriorate with vehicle.

Studies in mice looking at alpha-1 agonist therapy, using A61603, in a model of heart failure and cardiomyopathy due to myocardial infarction (heart attack). We used an animal model of myocardial infarction to test whether the alpha-1A agonist A61603 could rescue (e.g. treat) cardiomyopathy, when treatment was initiated at some time after injury (e.g. after the acute period was complete). Rescue mimics what is seen commonly in the clinic, where patients are admitted with HF, caused by a cardiomyopathy that has been present for months or years. This model was a model of ischemic, post-myocardial infarction (MI) cardiomyopathy. Ischemic heart disease caused by coronary atherosclerosis is extremely common and ischemic and overload cardiomyopathies associated with these diseases comprise the largest group of patients with HF. We used a mouse model of coronary ligation to cause MI. The mouse coronary ligation was permanent, however, patients typically have some form of reperfusion (e.g. angioplasty). We used a mouse model where the MI is healed completely, which is typical for patients admitted with HF late after MI. A61603 treatment rescued (e.g treated) the cardiomyopathy, as measured by heart function (FIG. 9A-B).

Figure 10:
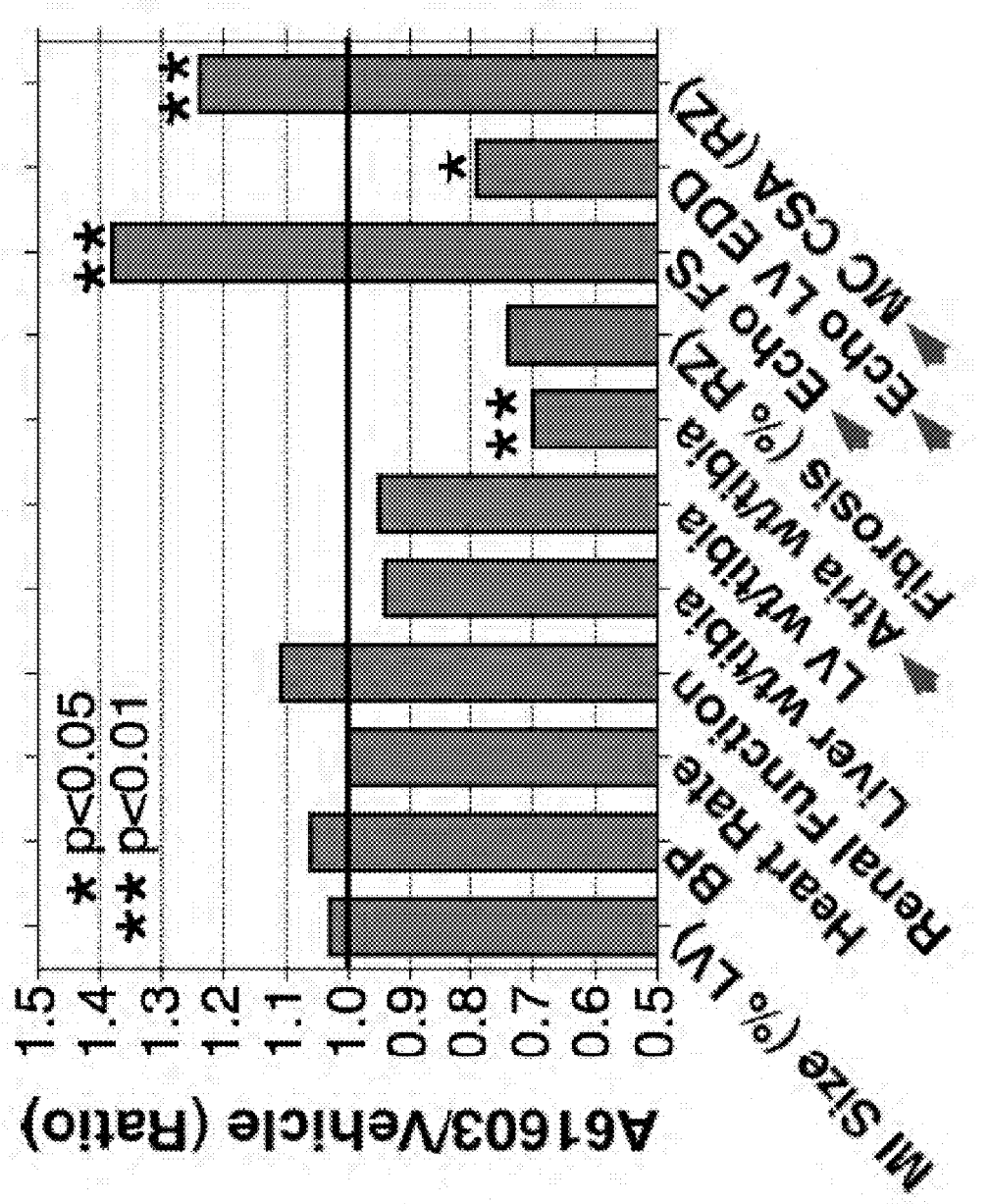
FIG. 10. A61603 in ischemic, post-MI cardiomyopathy improves growth and protection, and reduces fibrosis. Values are normalized to mice treated with vehicle. Mice treated with A61603 had smaller atria, less fibrosis, higher fractional shortening (FS), smaller left ventricle end diastolic diameter (LVEDD), and larger myocyte size in the surviving heart (MC CSA). The size of the MI was unchanged, as expected because treatment started 4 weeks after LAD ligation, by which time the MI had healed.

The improvement in function caused by A61603 after MI was again due to direct effects on ardiac muscle cells (FIG. 10). In this case, the effect was to increase the size of muscle cells in the surviving heart wall, helping restore the total amount of contracting heart muscle. There was also less fibrosis than control. The smaller weight of the atria indicates lower pressures within the left ventricle, a beneficial functional outcome, and the smaller diameter of the left ventricle indicates less cardiac enlargement, also a beneficial outcome.

In summary, the alpha-1A agonist A61603 at a low dose rescues cardiomyopathy due to ischemia (MI), a very common injury in cardiac disease, and the mechanism is improvement of cardiac myocytes. It is notable that myocyte size is larger with A61603 in the MI model, and smaller with A61603 in the pressure overload model, yet function is better in both, showing that alpha-1A agonist therapy causes beneficial growth, and reduces detrimental growth of heart muscle.

Right Ventricular Failure (from Pulmonary Hypertension)

Figure 11:
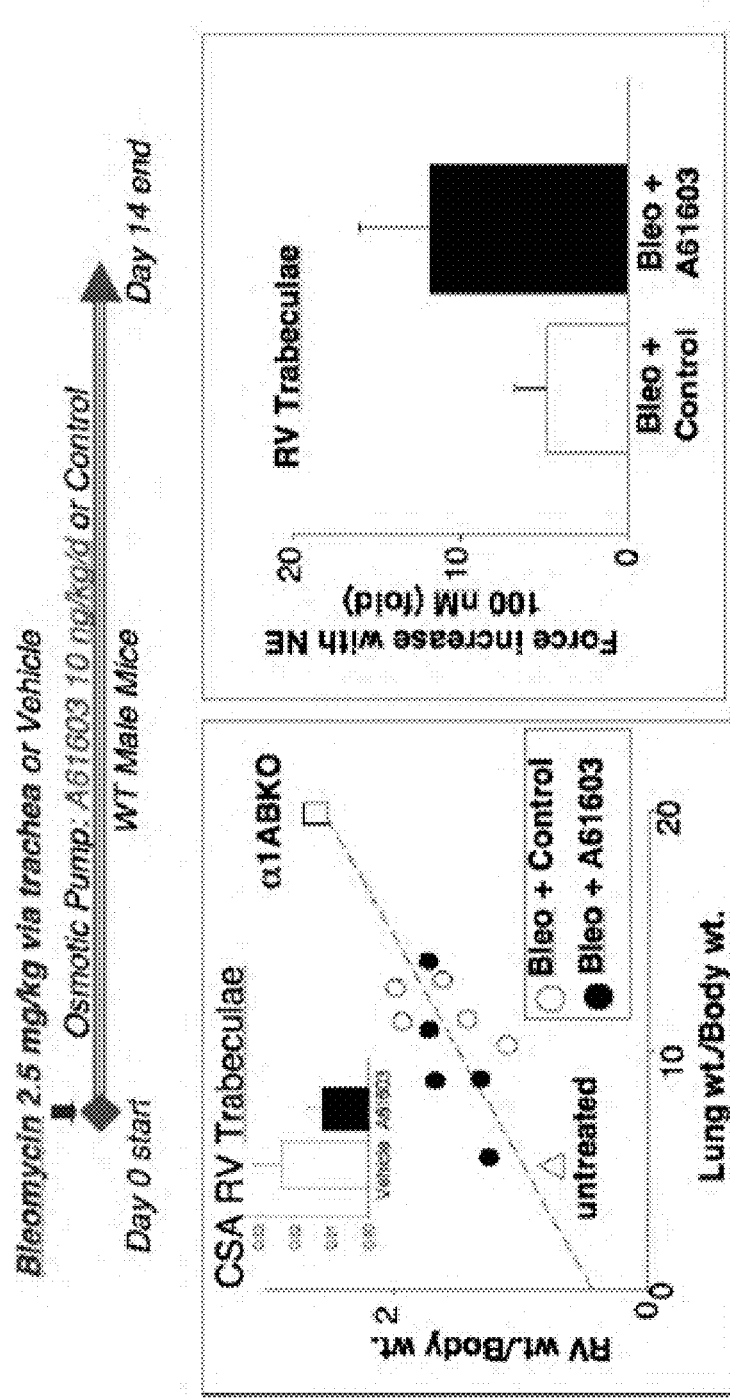
FIG. 11. A61603 reduces right ventricle (RV) cardiomyopathy in pulmonary hypertension. Mice had bleomycin instilled into the trachea and treatment with A61603 or vehicle. A61603 reduced or prevented RV failure, shown by the reduction of RV weight normalized to body weight. Mice with the alpha-1A knocked out did worse ($\alpha$1ABKO). Also, RV muscle taken from the treated mice and studied in vitro had better function if the mice were treated with A61603.
Figure 13:
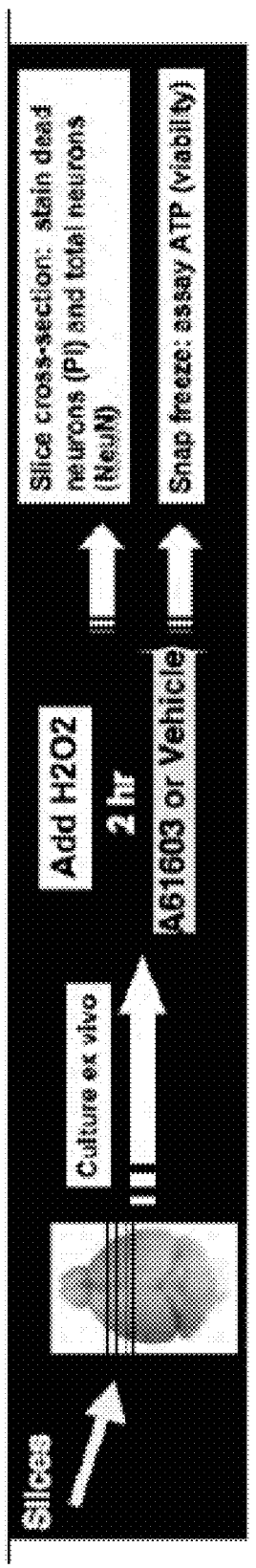
FIG. 13. Brain slice model to study alpha-1A agonist in vitro. Thin brain slices were injured with hydrogen peroxide ($H_2O_2$), which simulates most forms of ischemic and traumatic injury at the cell level, in the presence or absence of A61603. After 2 hr, dead neurons (PI) and living neurons (ATP) were measured.

Studies in mice looking at alpha-1 agonist therapy, using A61603, in a model of right ventricular failure from pulmonary hypertension. Failure of the right ventricle (RV) is a serious consequence of HF due to disease of the left ventricle (LV), and is also seen as an isolated problem, e.g. in lung disease (e.g. lung fibrosis), where treatment is extremely limited. Experiments were conducted with A61603 therapy in a mouse model of RV cardiomyopathy caused by pulmonary hypertension, which in turn was caused by lung fibrosis. Installation of bleomycin into the lung, caused fibrosis and secondary pulmonary hypertension and RV failure. Mice were treated continuously with A61603 or vehicle. A61603 at a low dose greatly improved the RV cardiomyopathy, shown by reduced RV failure and improved function of RV muscle in vitro (FIG. 11).

The alpha-1A agonist A61603 at a low dose prevents cardiomyopathy due to pulmonary hypertension caused by for example, pulmonary fibrosis. Even though the systemic and pulmonary vasculature are different in many ways known in the art, these results were similar to those seen with A61603 in the pressure overload model, which has systemic hypertension (FIG. 7-8).

Neuroprotection

Figure 14:
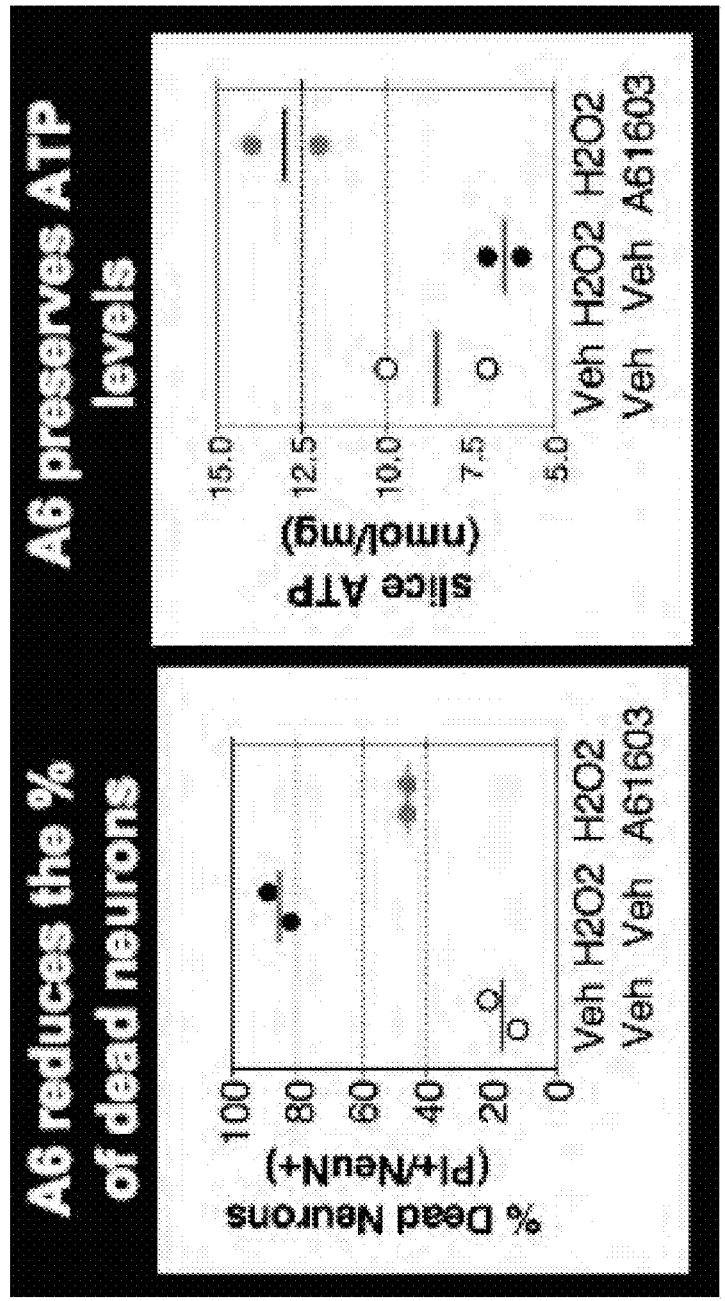
FIG. 14. A61603 protects neurons in brain slices from oxidative injury in vitro. Slices were treated with $H_2O_2$ or vehicle (Veh) for 2 hr, in the presence of A61603, or absence (Veh).

Studies were conducted in mice looking at alpha-1 agonist therapy, using A61603, in a model of traumatic brain injury. Alpha-1-ARs are 10 times more abundant in neurons than in cardiac myocytes, and the alpha-1A subtype is the most abundant. Studies were conducted to determine if the alpha-1A protected the brain, in the same way that it protected the heart. To study alpha-1A effects in vitro, we developed a model of thin slices from the adult mouse brain. Cultures of individual neurons can be established only from the fetal brain, which seemed less relevant, than adult brain slices. A61603 treatment during oxidative injury by $H_2O_2$ reduced dead neurons and increased viable neurons (FIG. 14).

The in vitro data showed that A61603 might be neuroprotective in vivo. To test this, we used a mouse model of traumatic brain injury (TBI), produced by a piston impact on the cerebral cortex, done through a hole in the skull. TBI is a clinical problem of great and growing importance.

Figure 15:
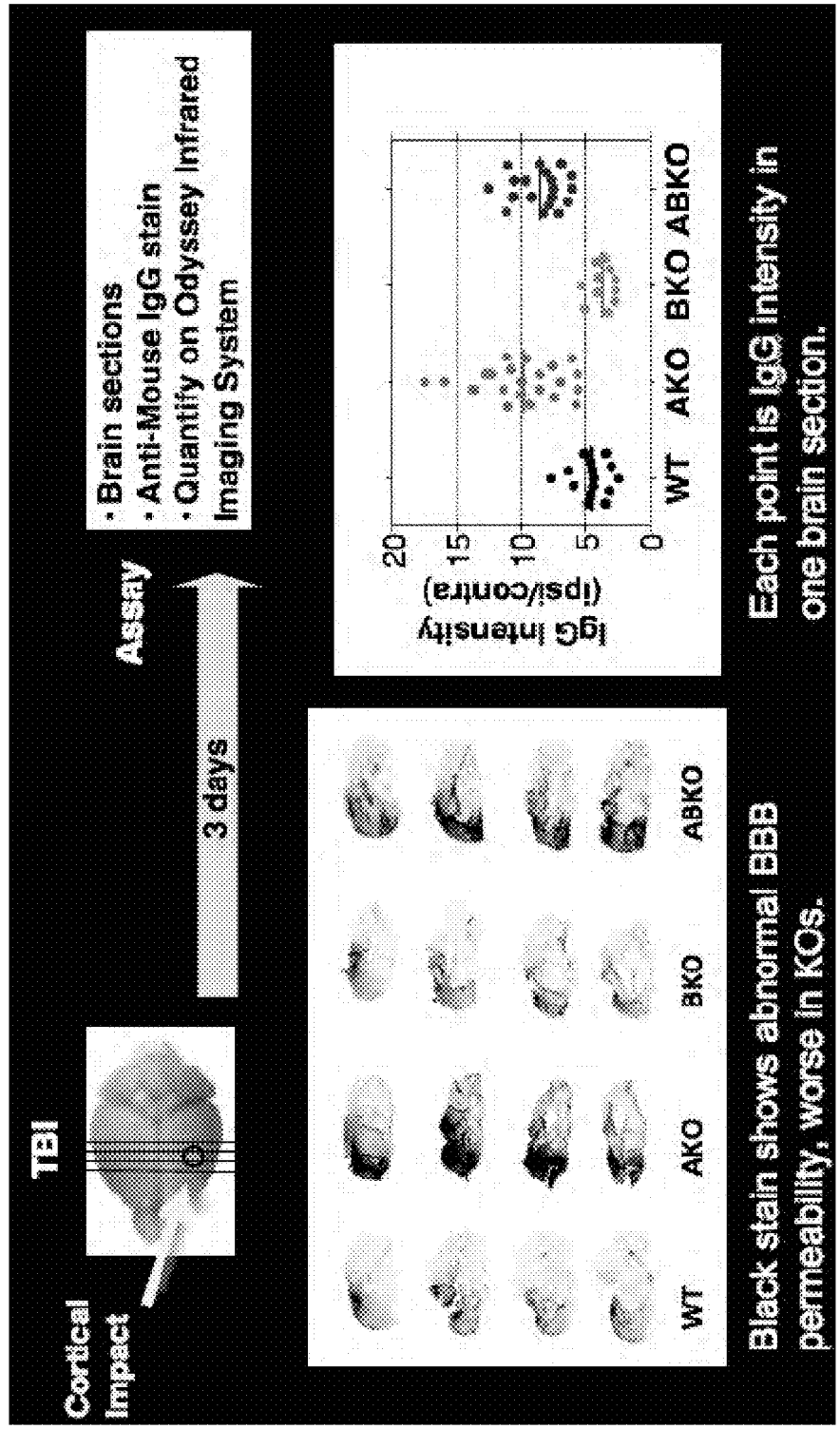
FIG. 15. KO of the alpha-1A worsens damage after TBI. Mice had TBI by cortical impact, and 3 days later damaged capillaries were measured by leakage of serum IgG into the brain tissue, showing that the blood brain barrier (BBB) was disrupted. The alpha-1A KO (AKO) and alpha-1AB double KO (ABKO) mice had worse damage than normal wild type mice (WT) or mice with alpha-1B KO (BKO).
Figure 16:
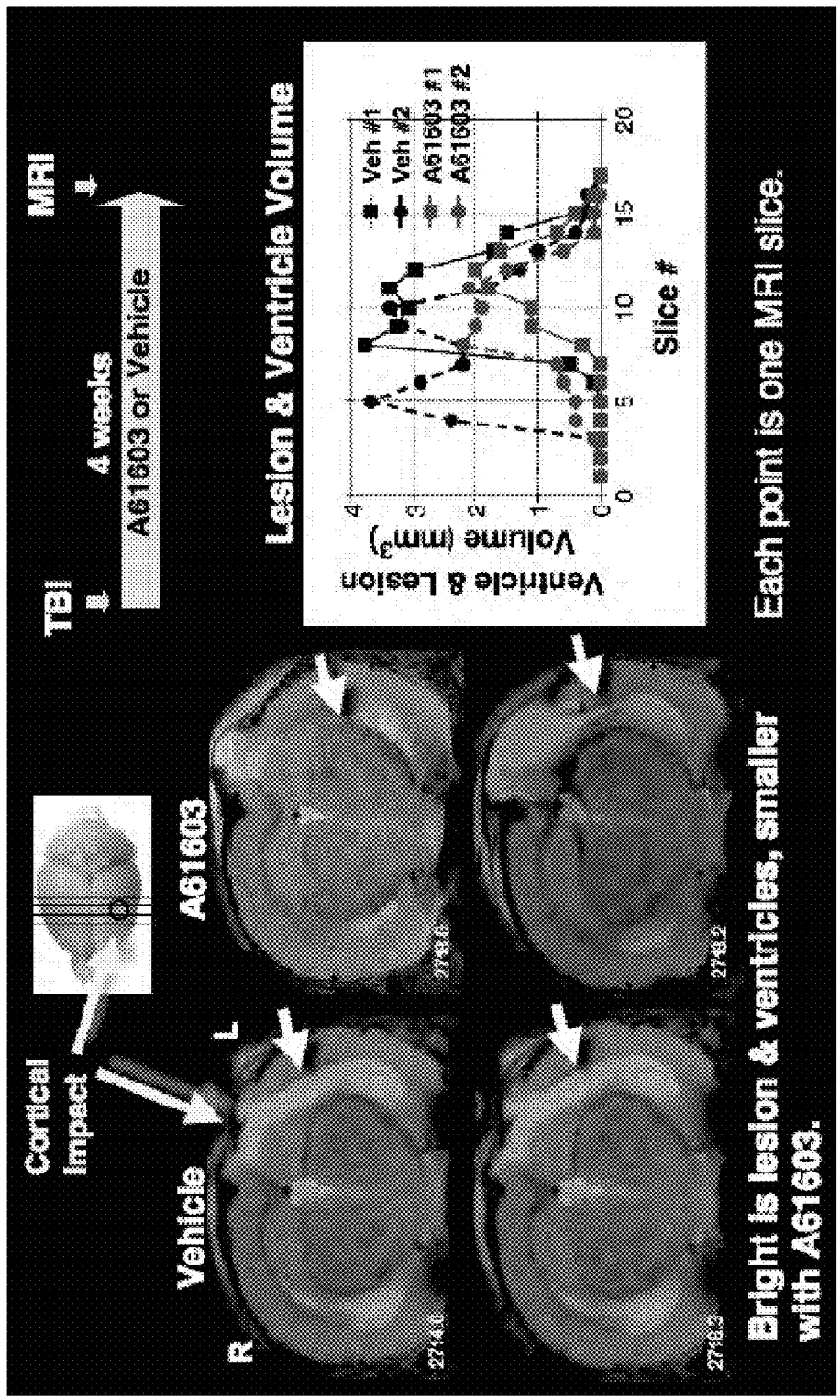
FIG. 16. The alpha-1A agonist A61603 reduces the amount of brain damage after TBI, quantified by MRI. Mice had TBI by cortical impact, followed by 4 weeks treatment with A61603 or vehicle. MRI was done to identify viable brain (dark) and fluid-filled areas of lost brain tissue (bright) (left). The volume of dead brain was 50% less with A61603 (red, right).

We tested the model in the alpha-1A knockout (KO) mouse. TBI in the alpha-1A KO caused the worst damage, compared with normal mice and mice with the alpha-1B KO (FIG. 15). We tested A61603 in normal wild type mice, using the same low BP-neutral dose employed in the cardiac studies, 10 ng/kg/d. The protocol was a prevention trial, and the end-point was magnetic resonance imaging (MRI), which can quantify the amount of dead and viable brain tissue in the living subject (e.g. mouse, human) non-invasively. A61603 reduced the amount of dead brain tissue after TBI (FIG. 16).

Figure 17:
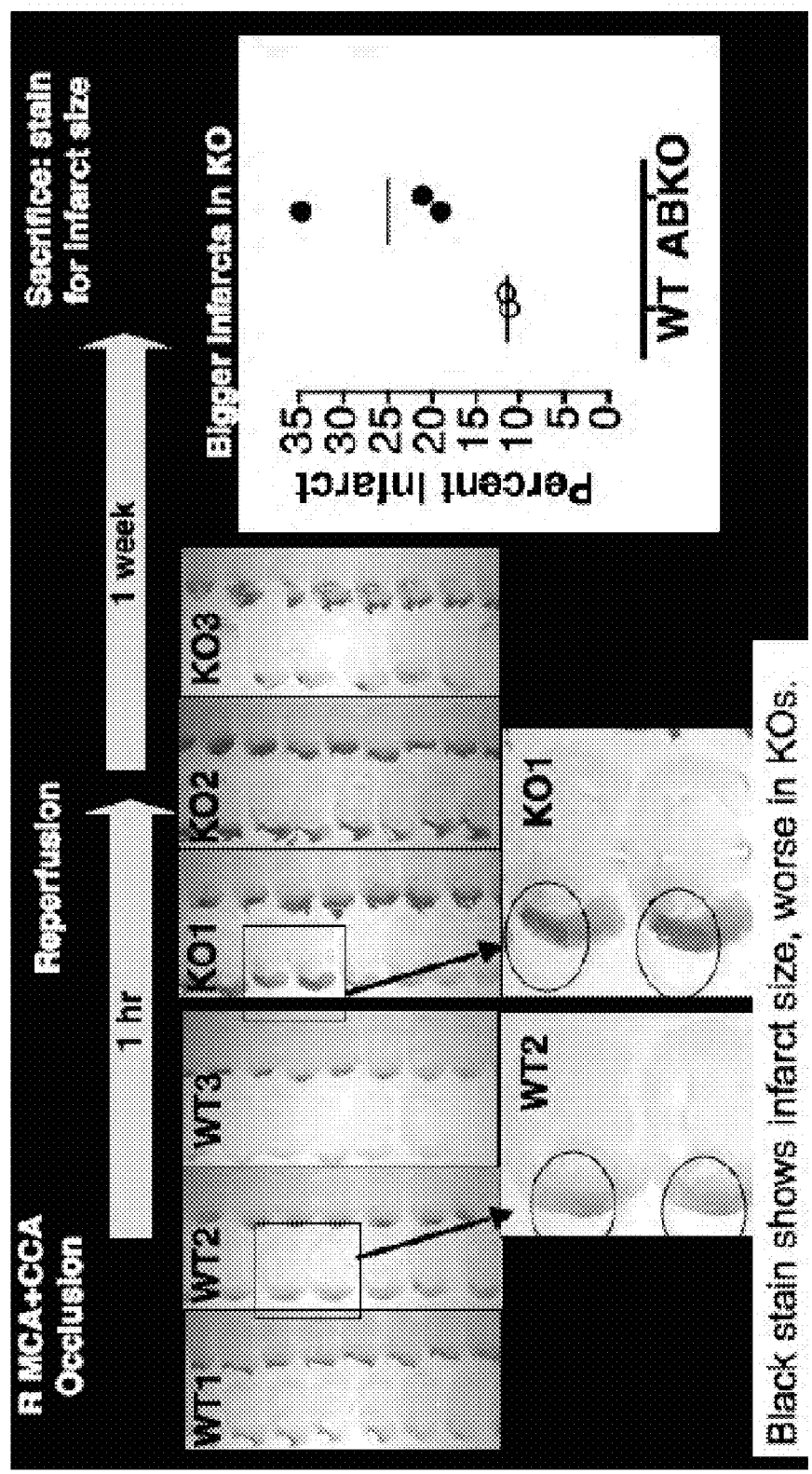
FIG. 17. Double KO of the alpha-1A and alpha-1B (ABKO) causes larger infarcts after IR. ABKO and WT mice matched for age and sex had 60 min occlusion of the right middle cerebral artery and the right common carotid artery, then reperfusion. Mice were injected i.p. with BrdU after surgery, to label proliferating cells. After 1 week, brains were fixed by trans-cardiac paraformaldehyde perfusion, and frozen section were used for immunohistochemistry for BrdU (DNA synthesis) and NeuN (neurons). Lett. BrdU. BrdU-labeled infarcts (dark) are larger in 3 ABKO mice than in 3 WT. Right. NeuN. NeuN staining indicates a larger percent infarct in the ipsilateral ABKO hemisphere.

Further characterization of neuroprotection by A61603, involves studies using ischemia-reperfusion (IR), a model for stroke. Double KO of the alpha-1A and alpha-1B increased the size of brain infarcts after IR (FIG. 17). The alpha-1A KO ischemia reperfusion experiment is being conducted to show alpha-1A KO is the reason for loss of neuroprotection (e.g. prevention of brain damage) compared to wildtype. Treatment of wildtype mice with A61603 in the model of stroke with ischemia-reperfusion is being conducted. In summary, the alpha-1A agonist A61603 protects neurons from oxidative damage and TBI. KO of the alpha-1A worsens brain damage in a TBI model and a stroke model, showing that alpha-1 (e.g. alpha-1A) agonists will treat or prevent brain damage from traumatic brain injury or stroke or related diseases or conditions. Experiments have shown that A61603 saves neurons in vivo and in vitro.

Figure 19:
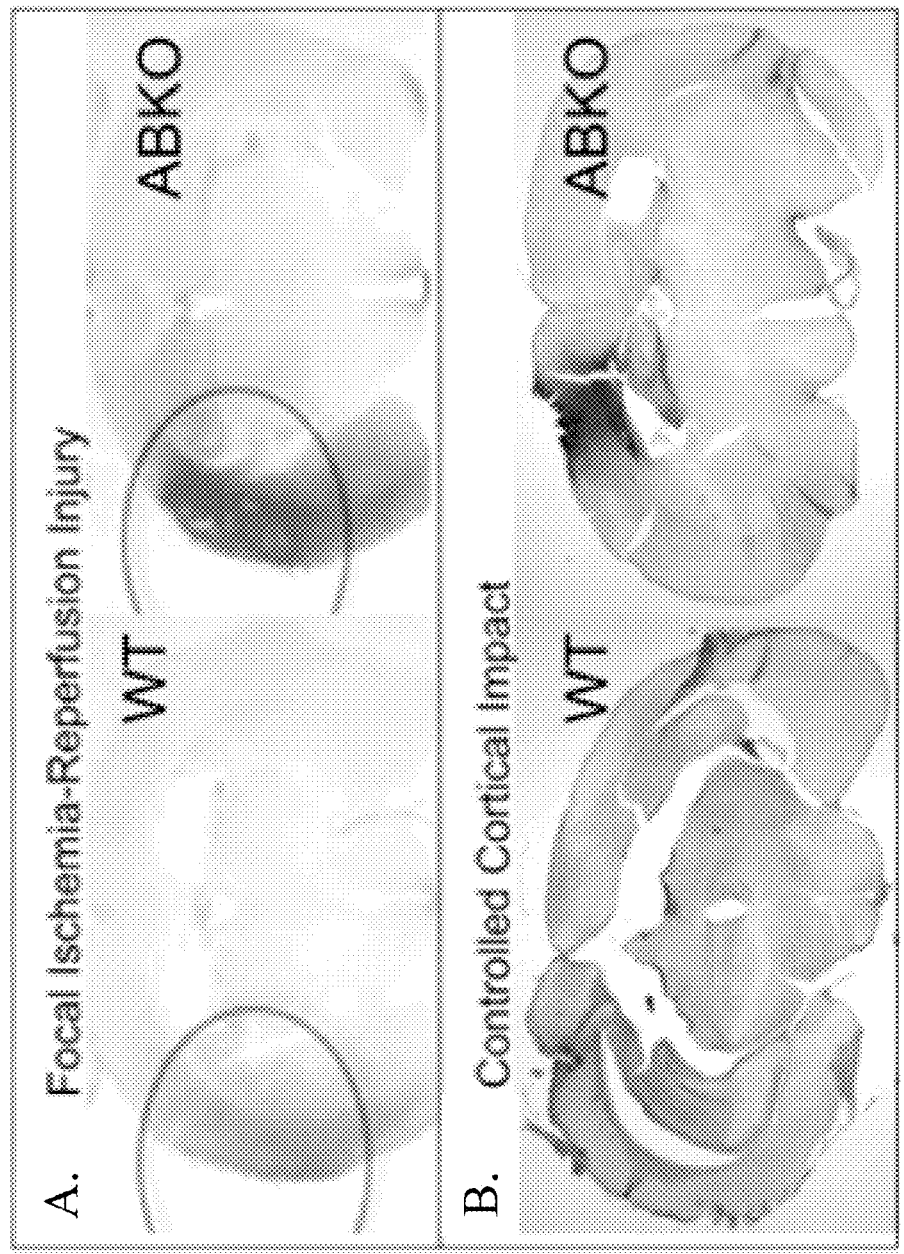
FIG. 19. A. Focal Ischemia-Reperfusion Injury, B. Controlled Cortical Impact.
Figure 20:
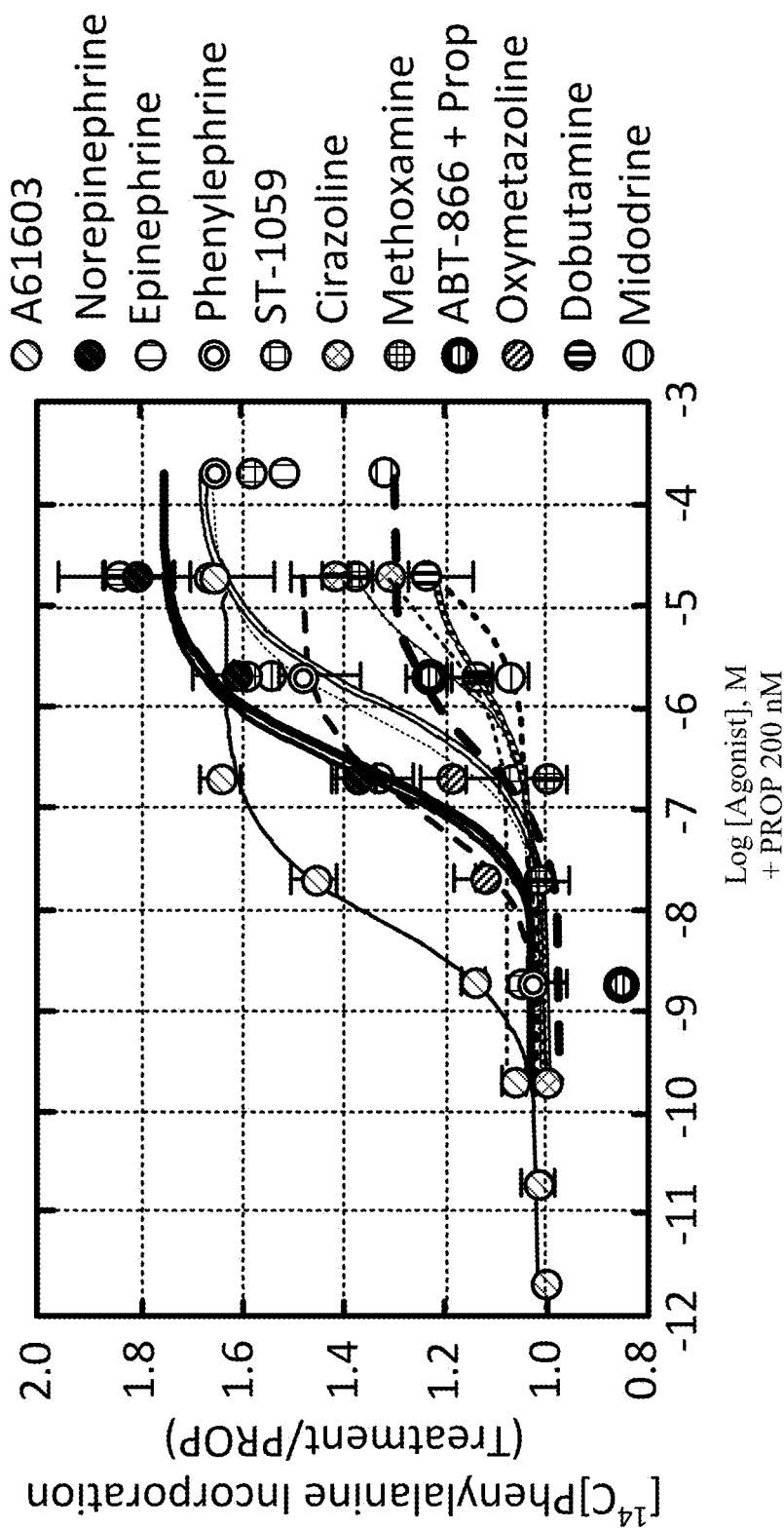
FIG. 20. A61603 is adaptive in cardiac muscle cells. A61603 activates protein synthesis, an anabolic, adaptive process, with high efficacy and potency, in cardiac muscle cells in vitro.

Alpha-1A-adrenergic receptors ($\alpha$1A-ARs) have a protective trophic role in the heart. $\alpha$1A-AR levels are high in the brain, and neuroprotection by norepinephrine is known. Recently, $\alpha$1A-ARs have been studied for their role in neurogenesis however, direct neuroprotection by $\alpha$1-AR subtypes is unclear. During ischemia or trauma $\alpha$1A-ARs on neurons mediate neuroprotection, analogous to cardioprotection. Ex vivo, we quantified ATP levels (marker for survival) in mouse brain slices injured by 10$\mu$, M $H_2O_2$ and treated for 2 h with A61603 (a1A-AR specific agonist) or Vehicle. We quantified the number of dead neurons (propidium iodide (PI) positive) out of total (NeuN positive) in the same treated slices by immunohistochemistry (IHC). In vivo, we measured brain infarct size (BrdU-positive glial cells) after transient focal ischemia and reperfusion (IR) in $\alpha$1ABKO and WT mice. Also, we measured by anti-mouse IgG IHC the levels of endogenous IgG extravasation (brain blood barrier (BBB) damage) after controlled cortical impact (CCI) in $\alpha$1ABKO and WT mice. In vivo, (FIG. 19A) infarct size in $\alpha$1ABKOs (N=3) was 2.1 times larger than in WT (N=2). Further, (FIG. 19B) endogenous IgG intensity (BBB damage) was also 2 fold increased in $\alpha$1ABKOs (N=2) compared with WT (N=2). Ex vivo, treatment with the $\alpha$1A agonist A61603 preserved ATP levels after $H_2O_2$ (8±1 vs. 5.5±0.5 nmol/mg protein, N=2). A61603 also reduced the number of dead neurons caused by $H_2O_2$ (46±0.3 vs. 86±5.3, N=2). $\alpha$1-ARs are required for brain protection in vivo during ischemic or traumatic injury, and the $\alpha$1A-AR subtype mediates neuron protection ex vivo from oxidative stress induced injury.

Learning and Memory

Initial studies in mice looking at alpha-1 agonist therapy, using cirazoline, to improve learning and memory in normal mice.

Initial studies using a different alpha-1A agonist, cirazoline, which is a good bit less potent and efficacious than is A61603, at least in cardiac myocytes (FIG. 1-2) were conducted. These studies treated mice for long periods with cirazoline, adding it to the drinking water. Mice treated with cirazoline had improvements in tests of learning and of memory (FIG. 18). Experiments with A61603, which is a more potent $\alpha$1-AR agonist than cirazoline are being conducted to show A61603 improves cognitive capabilities (e.g. learning or memory). alpha-1A agonist therapy improves brain function in normal mice with aging. 9 months in a mouse is equivalent to 18 to 27 years in a human.

The protective and treatment effects seen in the various brain damage models (e.g. TBI and IR) and the beneficial effects in ongoing cognitive capability models (e.g. learning or memory) show that alpha-1A agonist therapy, and specifically A61603 treatment or prophylaxis, may be useful in neurodegenerative disorders (e g Alzheimer's disease, Parkinson's disease, Huntingtin's disease, amyloid disease, dementia), or other conditions where higher cognitive function is impaired.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating brain damage in a patient in need of such treatment, said method comprising administering a therapeutically effective amount of A61603, or an analog, pharmaceutically acceptable salt, or prodrug thereof.

2. The method of claim 1, wherein said brain damage is associated with stroke, ischemia, neurodegenerative disease, or traumatic brain injury.

3. A method of improving one or more cognitive capabilities in a patient in need of such treatment, said method comprising administering an effective amount of A61603, or an analog, pharmaceutically acceptable salt, or prodrug thereof.

4. The method of claim 3, wherein said one more cognitive capabilities is selected from the group consisting of learning and memory.

5. The method of claim 1, wherein said brain damage is associated with stroke.

6. The method of claim 1, wherein said brain damage is associated with ischemia.

7. The method of claim 1, wherein said brain damage is associated with traumatic brain injury.

8. The method of claim 1, wherein said brain damage is associated with a neurodegenerative disease.

9. The method of claim 8, wherein said neurodegenerative disease is Alexander's disease, Alper's disease, Alzheimer's disease, Amyotrophic lateral sclerosis, Ataxia telangiectasia, Batten disease, Bovine spongiform encephalopathy, Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia, Spinal muscular atrophy, Steele-Richardson-Olszewski disease, or Tabes dorsalis.

10. The method of claim 8, wherein said neurodegenerative disease is Alzheimer's disease, Amyotrophic lateral sclerosis, Huntington's disease, Lewy body dementia, Parkinson's disease, or a Prion disease.

* * * * *